US012605434B2

(12) United States Patent

Christensen et al.

(10) Patent No.: US 12,605,434 B2
(45) Date of Patent: Apr. 21, 2026

(54) COMPOSITION FOR PREVENTING OR TREATING AUTOIMMUNE DISEASES

(71) Applicant: STATENS SERUM INSTITUT, Copenhagen (DK)

(72) Inventors: Dennis Christensen, Frederiksberg (DK); Jes Dietrich, Copenhagen (DK); Gabriel Pedersen, Charlottenlund (DK); Katharina Wørzner, Copenhagen (DK)

(73) Assignee: STATENS SERUM INSTITUT, Copenhagen (DK)

( * ) Notice: Subject to any disclaimer, the term of this patent is extended or adjusted under 35 U.S.C. 154(b) by 0 days.

(21) Appl. No.: 18/699,018

(22) PCT Filed: Sep. 13, 2022

(86) PCT No.: PCT/EP2022/075461
§ 371 (c)(1),
(2) Date: Apr. 5, 2024

(87) PCT Pub. No.: WO2023/057181
PCT Pub. Date: Apr. 13, 2023

(65) Prior Publication Data

US 2024/0398916 A1 Dec. 5, 2024

(30) Foreign Application Priority Data

Oct. 7, 2021 (EP) .................................... 21201523

(51) Int. Cl.

| | |
|---|---|
| *A61K 39/00* | (2006.01) |
| *A61K 39/39* | (2006.01) |
| *A61P 37/00* | (2006.01) |
| *C07K 14/705* | (2006.01) |
| *C07K 14/78* | (2006.01) |

(52) U.S. Cl.
CPC .......... *A61K 39/0008* (2013.01); *A61K 39/39* (2013.01); *A61P 37/00* (2018.01); *C07K 14/7056* (2013.01); *C07K 14/78* (2013.01); *A61K 2039/54* (2013.01); *A61K 2039/55505* (2013.01); *A61K 2039/55511* (2013.01)

(58) Field of Classification Search
None
See application file for complete search history.

(56) References Cited

PUBLICATIONS

Klemann et al, Japanese Journal of Clinical Immunology, 2009, vol. 32, Issue 1, pp. 20-28 (Year: 2009).*
Mucida et al., Science 317, 256-260 (2007) (Year: 2007).*
Yi Xianwen et al, Journal of Biomedical Nanotechnology, vol. 16, No. 4, Apr. 1, 2020 (Apr. 1, 2020), pp. 467-480 (Year: 2020).*
(Continued)

*Primary Examiner* — Karl J Puttlitz
(74) *Attorney, Agent, or Firm* — Howson & Howson, LLP; Kathleen D. Rigaut; Richard F. Kane

(57) ABSTRACT

The present invention relates to a composition for preventing or treating autoimmune diseases. In particular the present invention relates to a composition that prevents or treats the disease by specifically targeting the immune cells responsible for the autoimmune reaction. Thus one aspect relates to a composition comprising DDA and TDB or MMG, retinoic acid or analogues thereof, and at least one autoimmune antigen for use in prevention or treatment of autoimmune diseases.

17 Claims, 14 Drawing Sheets

Specification includes a Sequence Listing.

(56) References Cited

PUBLICATIONS

Hao Xinyan et al, The AAPS Journal, vol. 23, No. 2, Feb. 24, 2021 (Feb. 24, 2021) (Year: 2021).*
Christensen et al, ACS Nano, vol. 13, No. 2, Jan. 1, 2019 (Jan. 1, 2019), pp. 1116-1126 (Year: 2019).*
Pedersen Gabriel Kristian et al., Seminars in Immunology, vol. 39, Nov. 2, 2018 (Nov. 2, 2018), pp. 4-13 (Year: 2018).*
International Preliminary Report on Patentability, date completed Jan. 30, 2024, issued in corresponding International Application No. PCT/EP2022/075461. 14 pages.
Yi, Xianwen et al., "Retinoic Acid-Loaded PLGA Nanoparticle Formulation of ApoB-100-Derived Peptide 210 Attenuates Atherosclerosis," Journal of Biomedical Nanotechnology, vol. 16, No. 4, Apr. 2020, pp. 467-480.
International Search Report, date mailed Feb. 7, 2023, issued in corresponding International Application No. PCT/EP2022/075461. 3 pages.
Written Opinion of the International Preliminary Examining Authority, date mailed Aug. 21, 2023, issued in corresponding International Application No. PCT/EP2022/075461. 9 pages.
Christensen, Dennis et al., "A Liposome-Based Adjuvant Containing Two Delivery Systems with the Ability to Induce Mucosal Immunoglobulin A Following a Parenteral Immunization," ACS Nano, vol. 13, No. 2, Jan. 2019, pp. 1116-1126.
Pedersen, Gabriel Kristian et al., "Immunocorrelates of CAF family adjuvants," Seminars in Immunology, W.B. Saunders Company, PA, US, vol. 39, Nov. 2018, pp. 4-13.
Hao, Xinyan et al., "The effects of all-trans retinoic acid on immune cells and its formulation design for vaccines," The AAPS Journal, vol. 23, No. 2: 32, Feb. 2021, pp. 1-8.

* cited by examiner

H

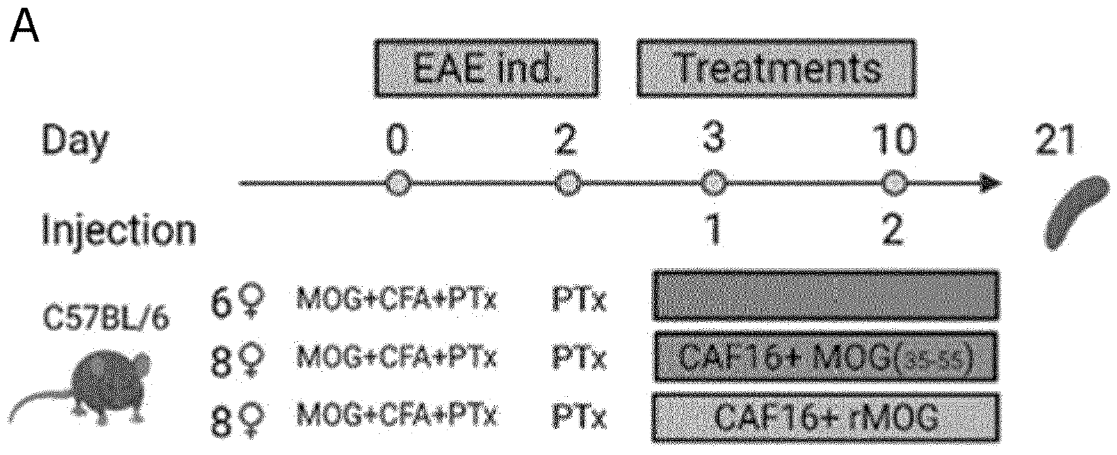
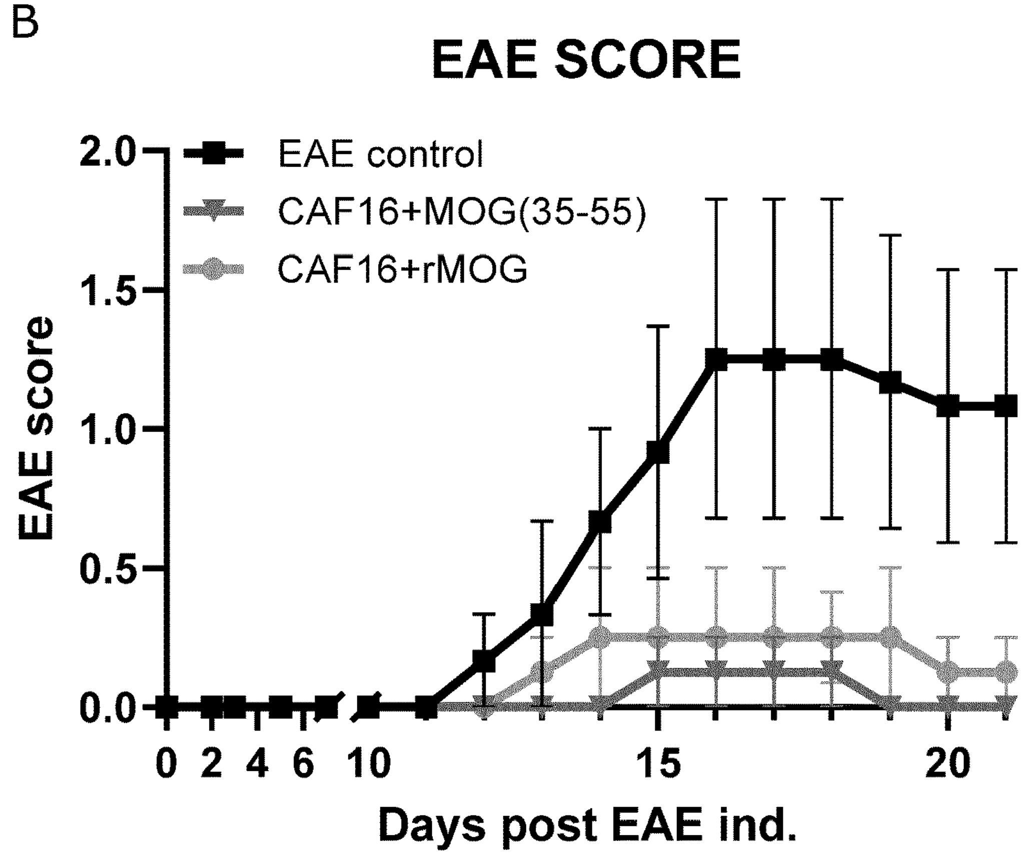
Fig. 8A-B

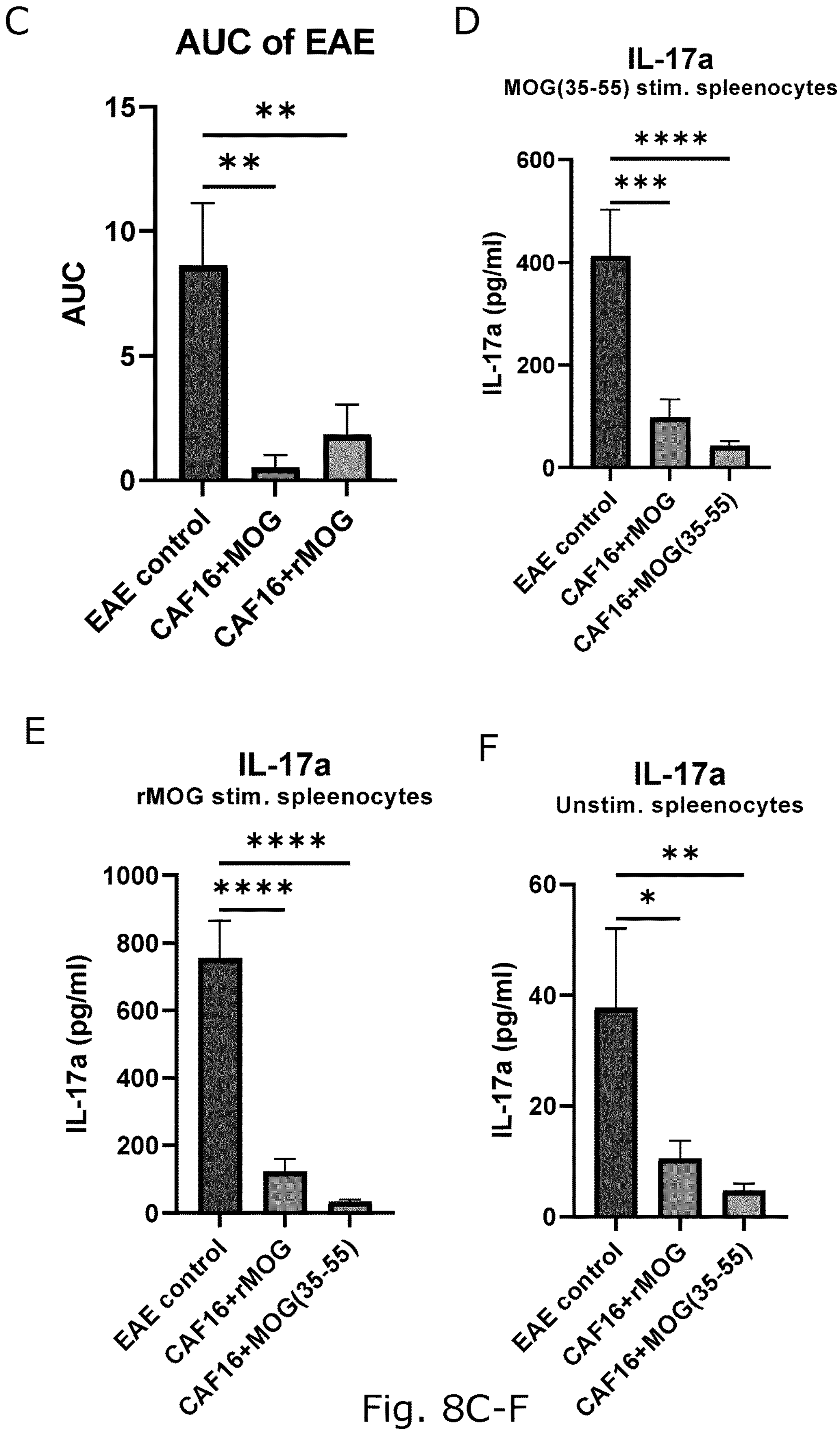
Fig. 8C-F

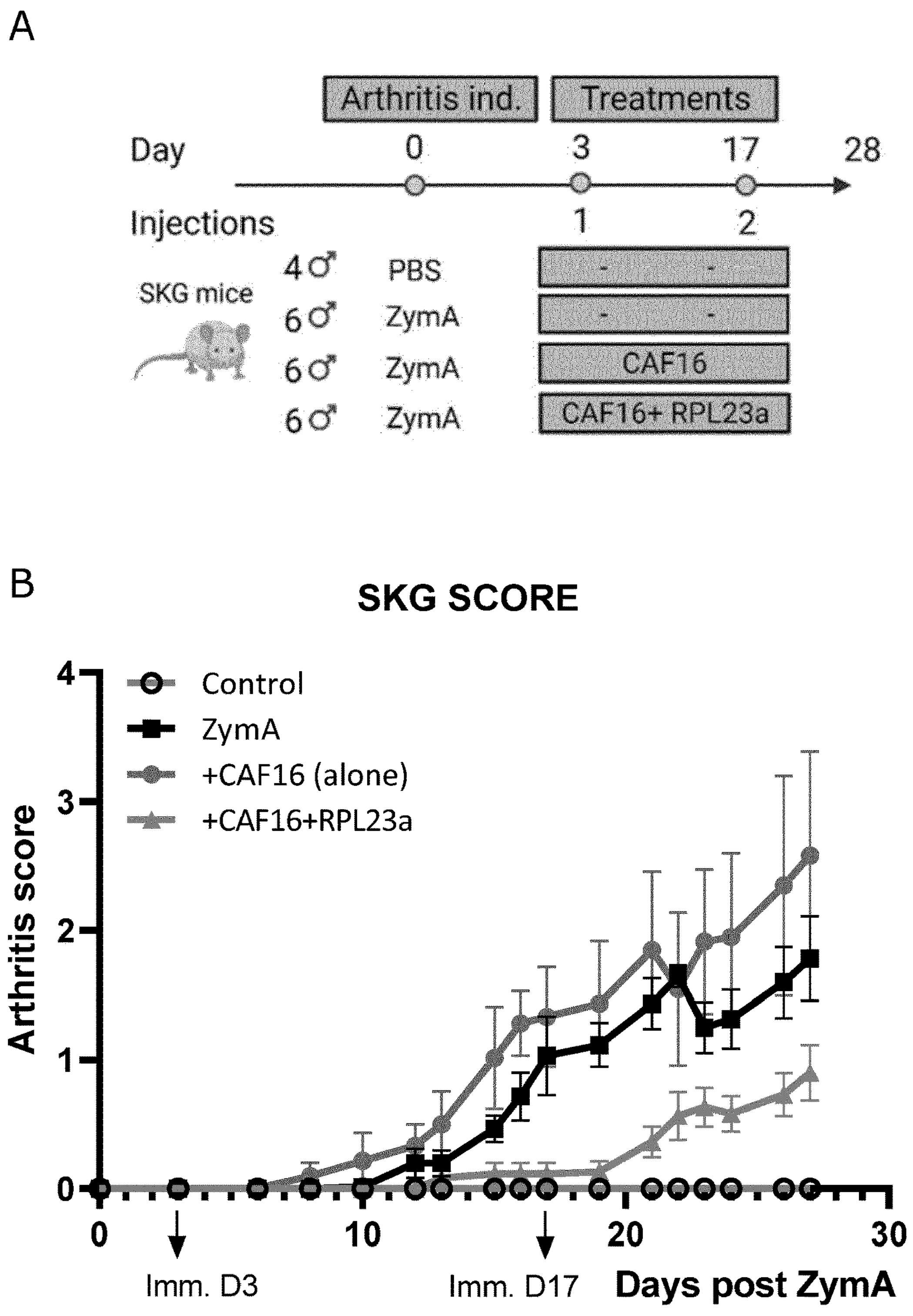
Fig. 9A-B

C

SEQUENCE LISTING

```
Sequence total quantity: 7
SEQ ID NO: 1           moltype = AA  length = 457
FEATURE                Location/Qualifiers
REGION                 1..457
                       note = -
source                 1..457
                       mol_type = protein
                       organism = synthetic construct
SEQUENCE: 1
MKFSRPGLPV EYLQVPSPSM GRDIKVQFQS GGNNSPAVYL LDGLRAQDDY NGWDINTPAF  60
EWYYQSGLSI VMPVGGQSSF YSDWYSPACG KAGCQTYKWE TFLTSELPQW LSANRAVKPT  120
GSAAIGLSMA GSSAMILAAY HPQQFIYAGS LSALLDPSQG MGPSLIGLAM GDAGGYKAAD  180
MWGPSSDPAW ERNDPTQQIP KLVANNTRLW VYCGNGTPNE LGGANIPAEF LENFVRSSNL  240
KFQDAYNAAG GHNAVFNFPP NGTHSWEYWG AQLNAMKGDL QSSLGAGMTE QQWNFAGIEA  300
AASAIQGNVT SIHSLLDEGK QSLTKLAAAW GGSGSEAYQG VQQKWDATAT ELNNALQNLA  360
RTISEAGQAM ASTEGNVTGM FAVIAGVDQA LAATGQASQR AAGASGGVTV GVGVGTEQRN  420
LSVVAPSQFT FSSRSPDFVD ETAGQSWCAI LGLNQFH                          457

SEQ ID NO: 2           moltype = AA  length = 507
FEATURE                Location/Qualifiers
REGION                 1..507
                       note = -
source                 1..507
                       mol_type = protein
                       organism = synthetic construct
SEQUENCE: 2
MHHHHHHDAI SMRVGYYGDF VFDRVLKTDV NKEFQMGAKP TTDTGNSAAP STLTARENPA  60
YGRHMQDAEM FTNAASMALN IWDRFDVFST LGATSGYLKG NSASFNLVGL FGDNENQKTV  120
KAESVPNMSF DQSVVELYTD TTFAWSVGAR AALWESGSAT LGASFQYAQS KPKVEELNVL  180
SNAAEFTINK PKGYVGKEFP LDLTAGTDAA TGTKDASIDY HEWQASLALS YRLNMFTPYI  240
GVKWSRASFD ADTIRIAQPK SATAIFDTTT LNPTIAGAGD VKTGAEGQLG DTMQIVSLQL  300
NNMFTPYIGV KWSRASFDAD TIRIAQPKSA TAIFDTTTLN PTIAGAGDVK ASAEGQLGDT  360
MQIVSLQLNN MFTPYIGVKW SRASFDSDTI RIAQPRLVTP VVDITTLNPT IAGSGSVAGA  420
NTEGQISDTM QIVSLQLNNM FTPYIGVKWS RASFDSNTIR IAQPKLAKPV VDITTLNPTI  480
AGSGSVVAAN SEGQISDTMQ IVSLQLN                                     507

SEQ ID NO: 3           moltype = AA  length = 1487
FEATURE                Location/Qualifiers
REGION                 1..1487
                       note = -
source                 1..1487
                       mol_type = protein
                       organism = synthetic construct
SEQUENCE: 3
MIRLGAPQSL VLLTLLIAAV LRCQGQDAQE AGSCLQNGQR YKDKDVWKPS SCRICVCDTG  60
NVLCDDIICE DPDCLNPEIP FGECCPICPA DLATASGKLG PKGQKGEPGD IRDIIGPRGP  120
PGPQGPAGEQ GPRGDRGDKG EKGAPGPRGR DGEPGTPGNP GPAGPPGPPG PPGLSAGNFA  180
AQMAGGYDEK AGGAQMGVMQ GPMGPMGPRG PPGPAGAPGP QGFQGNPGEP GEPGVSGPMG  240
PRGPPGPAGK PGDDGEAGKP GKSGERGLPG PQGARGFPGT PGLPGVKGHR GYPGLDGAKG  300
EAGAPGVKGE SGSPGENGSP GPMGPRGLPG ERGRTGPAGA AGARGNDGQP GPAGPPGPVG  360
PAGGPGFPGA PGAKGEAGPT GARGPEGAQG SRGEPGNPGS PGPAGASGNP GTDGIPGAKG  420
SAGAPGIAGA PGFPGPRGPP GPQGATGPLG PKGQAGEPGI AGFKGDQGPK GETGPAGPQG  480
APGPAGEEGK RGARGEPGGA GPIGPPGERG APGNRGFPGQ DGLAGPKGAP GERGPSGLTG  540
PKGANGDPGR PGEPGLPGAR GLTGRPGDAG PQGKVGPSGA PGEDGRPGPP GPQGARGQPG  600
VMGFPGPKGA NGEPGKAGEK GLAGAPGLRG LPGKDGETGA AGPPGPSGPA GERGEQGAPG  660
PSGFQGLPGP PGPPGEGGKQ GDQGIPGEAG APGLVGPRGE RGFPGERGSP GAQGLQGPRG  720
LPGTPGTDGP KGAAGPDGPP GAQGPPGLQG MPGERGAAGI AGPKGDRGDV GEKGPEGAPG  780
KDGGRGLTGP IGPPGPAGAN GEKGEVGPPG PSGSTGARGA PGERGETGPP GPAGFAGPPG  840
ADGQPGAKGD QGEAGQKGDA GAPGPQGPSG APGPQGPTGV TGPKGARGAQ GPPGATGFPG  900
AAGRVGPPGA NGNPGPAGPP GPAGKDGPKG VRGDSGPPGR AGDPGLQGPA GAPGEKGEPG  960
DDGPSGLDGP PGPQGLAGQR GIVGLPGQRG ERGFPGLPGP SGEPGKQGAP GASGDRGPPG  1020
PVGPPGLTGP AGEPGREGSP GADGPPGRDG AAGVKGDRGE TGALGAPGAP GPPGSPGPAG  1080
PTGKQGDRGE AGAQGPMGPS GPAGARGIAG PQGPRGDKGE SGEQGERGLK GHRGFTGLQG  1140
LPGPPGPSGD QGASGPAGPS GPRGPPGPVG PSGKDGSNGI PGPIGPPGPR GRSGETGPVG  1200
PPGSPGPPGP PGPPGPGIDM SAFAGLGQRE KGPDPMQYMR ADEADSTLRQ HDVEVDATLK  1260
SLNNQIESIR SPDGSRKNPA RTCQDLKLCH PEWKSGDYWI DPNQGCTLDA MKVFCNMETG  1320
ETCVYPNPAT VPRKNWWSSK SKEKKHIWFG ETMNGGFHFS YGDGNLAPNT ANVQMTFLRL  1380
LSTEGSQNIT YHCKNSIAYL DEAAGNLKKA LLIQGSNDVE MRAEGNSRFT YTALKDGCTK  1440
HTGKWGKTVI EYRSQKTSRL PIIDIAPMDI GGAEQEFGVD IGPVCFL               1487

SEQ ID NO: 4           moltype = AA  length = 246
FEATURE                Location/Qualifiers
source                 1..246
                       mol_type = protein
                       organism = Mus musculus
SEQUENCE: 4
MACLWSFSWP SCFLSLLLLL LQLSCSYAGQ FRVIGPGYPI RALVGDEAEL PCRISPGKNA  60
TGMEVGWYRS PFSRVVHLYR NGKDQDAEQA PEYRGRTELL KETISEGKVT LRIQNVRFSD  120
```

-continued

```
EGGYTCFFRD HSYQEEAAME LKVEDPFYWV NPGVLTLIAL VPTILLQVPV GLVFLFLQHR  180
LRGKLRAEVE NLHRTFDPHF LRVPCWKITL FVIVPVLGPL VALIICYNWL HRRLAGQFLE  240
ELRNPF                                                             246

SEQ ID NO: 5           moltype = AA  length = 125
FEATURE                Location/Qualifiers
source                 1..125
                       mol_type = protein
                       organism = Mus musculus
SEQUENCE: 5
GQFRVIGPGY PIRALVGDEA ELPCRISPGK NATGMEVGWY RSPFSRVVHL YRNGKDQDAE  60
QAPEYRGRTE LLKETISEGK VTLRIQNVRF SDEGGYTCFF RDHSYQEEAA MELKVEDPFY  120
WVNPG                                                              125

SEQ ID NO: 6           moltype = AA  length = 21
FEATURE                Location/Qualifiers
source                 1..21
                       mol_type = protein
                       organism = Mus musculus
SEQUENCE: 6
MEVGWYRSPF SRVVHLYRNG K                                            21

SEQ ID NO: 7           moltype = AA  length = 156
FEATURE                Location/Qualifiers
source                 1..156
                       mol_type = protein
                       organism = Mus musculus
SEQUENCE: 7
MAPKAKKEAP APPKAEAKAK ALKAKKAVLK GVHSHKKKKI RTSPTFRRPK TLRLRRQPKY  60
PRKSAPRRNK LDHYAIIKFP LTTESAMKKI EDNNTLVFIV DVKANKHQIK QAVKKLYDID  120
VAKVNTLIRP DGEKKAYVRL APDYDALDVA NKIGII                            156
```

COMPOSITION FOR PREVENTING OR TREATING AUTOIMMUNE DISEASES

CROSS-REFERENCE OF RELATED APPLICATIONS

This application is a § 371 of International Application No. PCT/EP2022/075461, filed Sep. 13, 2022, which claims the benefit of priority to EP Provisional Application Ser. No. 21201523.4, filed Oct. 7, 2021, each of which are incorporated by reference in their entirety.

INCORPORATION-BY-REFERENCE OF MATERIAL SUBMITTED IN ELECTRONIC FORM

The Contents of the electronic sequence listing (SequenceListing.xml; Size: 10,915 bytes; and Date of Creation: Apr. 3, 2024) is herein incorporated by reference in its entirety.

TECHNICAL FIELD OF THE INVENTION

The present invention relates to a composition for preventing or treating autoimmune diseases. In particular the present invention relates to a composition that prevents or treats the disease by specifically targeting the immune cells responsible for the autoimmune reaction.

BACKGROUND OF THE INVENTION

The role of the immune system is to protect the host against foreign invaders such as bacteria, viruses and fungi. However, problems with inducing tolerance in the body can lead to autoimmune diseases, where the immune system attacks the body's own cells. Rheumatoid arthritis (RA) and Multiple Sclerosis (MS) are two of the most common autoimmune diseases and the current treatment against these are immunosuppressive agents that often have many side effects and leave the patient immunocompromised. A commonality of these two diseases is that Th17 cells play an important role.

In RA, the immune system attacks the synovium surrounding the joints. The infiltration of inflammatory cells into the joints leads to chronic cartilage destruction. RA occurs in 0.5-1.0% of the adult population in industrialized countries, and 5-20% of RA patients are difficult to treat even when treated according to European League Against Rheumatism (EULAR) recommendations. Several studies have documented the increased presence of $CD4^+$ Th17 cells and/or its primary secreted cytokine; IL-17a in both the blood and in inflamed joints of people with RA. This is furthermore supported by experimental models of arthritis in mice, and through human in vitro experiments.

MS is a chronic inflammatory disease with destruction of the myelin shift in the central nervous system. Approx. 3 million people are estimated to live with MS and the prognosis is very poor with a life expectancy of 25-35 years after disease onset. Th17 cells have been reported to disrupt the junction proteins in the endothelial cells of the central nervous system and migrate through the brain blood barrier. Furthermore, studies have shown that Th17 cells accumulate in the cerebrospinal fluid of MS patients and an increased percentage of circulating Th17 cells have been observed in people with more severe MS. It has been demonstrated that the IL-17 level is increased in MS patients and that Th17 cells are present in human MS brain tissue.

The above mentioned disease are the most evident ones, but several other autoimmune diseases have been connected with elevated IL17a/Th17 cells including Systemic Lupus Erythematosus (SLE), Juvenile idiopathic arthritis (JIA), Sjögren syndrome, Systemic Sclerosis (SSc), alzheimers disease ankylosing spondylitis (AS), Type 1 Diabetes (T1D), Autoimmune thyroid diseases (AITD) such as Graves' disease and Hashimoto's disease, Myasthenia Gravis, Inflammatory Bowel Diseases (IBDs) such as Crohn's disease and ulcerative colitis and Psoriasis.

Nevertheless, targeting and blocking IL-17a in RA patients have shown discouraging results in clinical trials. A phase II clinical trial in MS patients targeting the Th17 pathway did also not improve disease progression. Th17 cell are plastic and can change their transcriptional profile into other types of cells, such as FoxP3 regulatory T cells (Tregs) or $IL\text{-}10^+$ Tr1 cells, which is why targeting existing Th17 cells is a desirable therapy in the fight against Th17-driven/mediated autoimmune diseases.

Realizing that Th17 cells also play an important role in the protection against infectious diseases, inhibiting the entire Th17 population would be a disadvantage for the patients.

Hence, a composition which is able to specifically inhibit, eliminate or transdifferentiate those Th17 cells that are Auto-antigen (AutoAg) specific for the given disease, into less harmful T cell subsets, while not inhibiting the protective Th17 cells, would be an advantage.

SUMMARY OF THE INVENTION

Thus, an object of the present invention relates to the provision of a composition for prevention or treatment of a autoimmune disease.

In particular, it is an object of the present invention to provide a composition that solves the above mentioned problems of the prior art.

Thus, one aspect of the invention relates to a composition comprising DDA, TDB and/or MMG, retinoic acid or analogues thereof, and at least one autoimmune antigen for use in prevention or treatment of autoimmune diseases.

In one embodiment of the invention, the composition comprises TDB and MMG.

In another embodiment of the invention, the composition comprises DDA, TDB, retinoic acid or analogues thereof, and at least one autoimmune antigen.

In a further embodiment of the invention, the composition comprises DDA, MMG, retinoic acid or analogues thereof, and at least one autoimmune antigen.

In yet another embodiment of the invention, the composition further comprises cholesterol, preferably in an amount of 2000 μg/ml.

In one embodiment, the autoimmune disease is a Th17 cell mediated autoimmune disease.

In another embodiment, the autoimmune disease is selected from the group consisting of Rheumatoid arthritis (RA), Multiple Sclerosis (MS), Systemic Lupus Erythematosus (SLE), Juvenile idiopathic arthritis (JIA), Sjögren syndrome, Systemic Sclerosis (SSc), ankylosing spondylitis (AS), Type 1 Diabetes (T1D), Autoimmune thyroid diseases (AITD) such as Graves' disease and Hashimoto's disease, Myasthenia Gravis, Inflammatory Bowel Diseases (IBDs) such as Crohn's disease and ulcerative colitis and Psoriasis, preferably the autoimmune diseases is Rheumatoid arthritis (RA) or Multiple Sclerosis (MS).

BRIEF DESCRIPTION OF THE FIGURES

FIG. 8 shows the effect of CAF®16 on disease scores and secretion of IL-17a in the experimental allergic encephalomyelitis (EAE) autoimmune disease model mimicking Multiple Sclerosis in humans. A) Experimental setup. EAE was induced on day 0 by injection of a CFA-MOG emulsion s.c. at four different locations. Pertussis Toxin (PTx) was injected i.p. on day 0 and 2. Mice were either treated with nothing (n=6) or with CAF®16 with either the MOG (35-55) peptide (n=8) or MOG (1-125) recombinant human protein (rMOG) (n=8) as a s.c. injection on day 3 and 10. The experiment was terminated at day 21 where spleens where harvested. B) EAE disease scores. Mice were scored based on their clinical signs wherein score 0: clinically normal, 1: weak tail, and 2: weak hind limbs 3: one hind limb paralyzed, 3.5: both hind limbs paralyzed, 4: both hind limbs paralyzed and weak front limbs, 4.5: Both hind limbs and one front limb paralyzed, or non-functional movement, 5: Both hindlimbs and both front limbs paralyzed, and/or moribund. C) The area under the curve of the EAE disease scores for the treated groups and a control group. Spleens were harvested and stimulated with either MOG (35-55) (D), rMOG (E) or no antigens (F) for three days at 37° C., and the supernatants were investigated using IL-17a ELISA.

Figure 1:
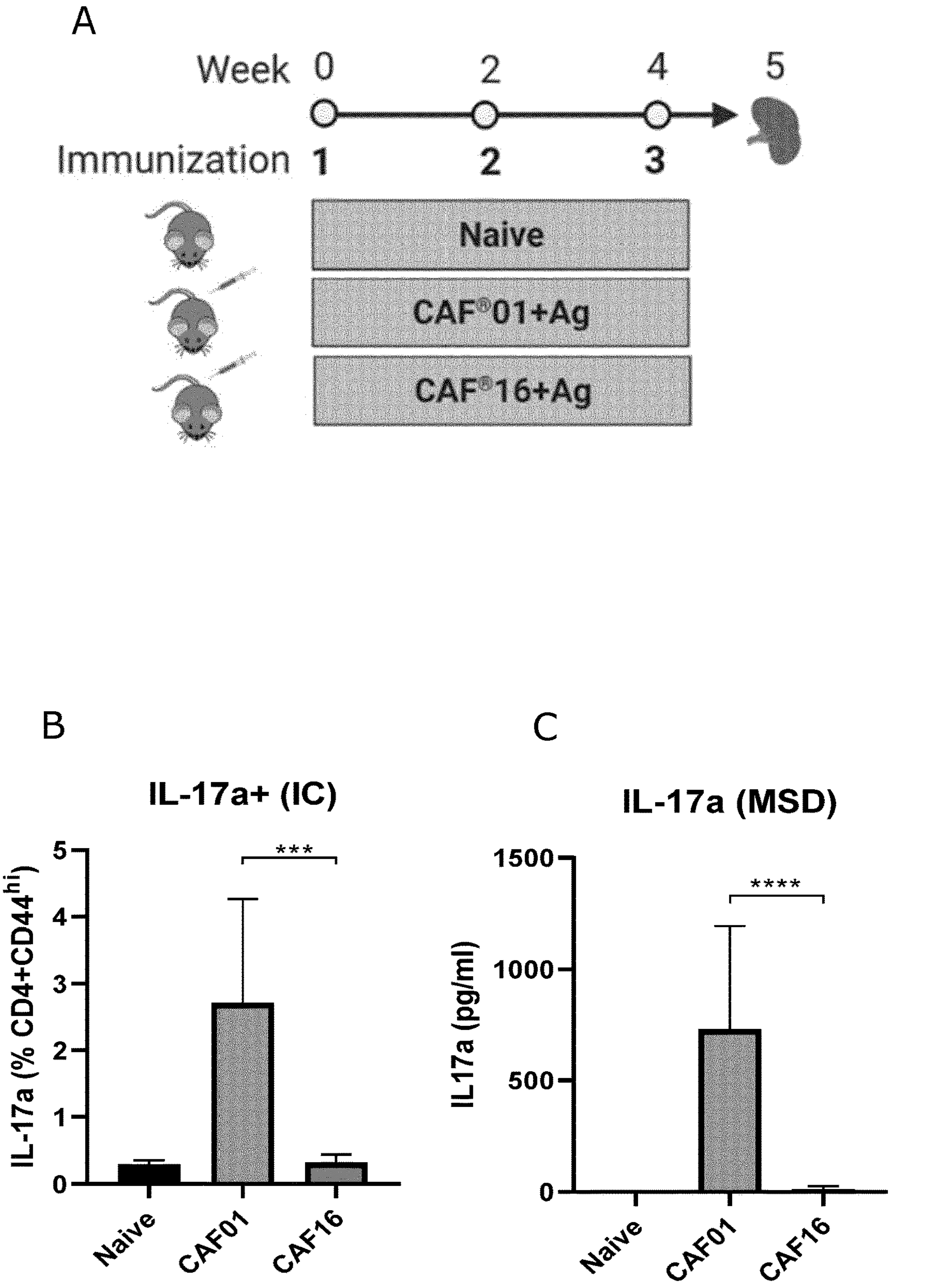
FIG. 1 shows that incorporating ATRA in CAF®01 completely abrogates inflammatory T cell responses and increases anti-inflammatory IL-10 but does not abrogate Ag specific T cell induction. A) Experiment setup; spleenocytes from female C57BL/6 mice were harvested 10 days post s.c. immunizations with three times 200 μl 5 μg Ag/dose vaccine measured with intracellular flow cytometry (IC) of cells stimulated for 6 h with the antigen or with electrochemoluminiscence assay by MSD of supernatants from splenocytes restimulated with Ag for three days. B) IL-17a (IC), C) IL-17a (MSD), D) IFN-γ (IC), E) IFN-γ (MSD), F) IL-10 (MSD). G) and H) MHCII tetramers surface staining (FACS) on antigen-specific cells. Statistical analysis was performed using an unpaired Mann-Whitney t-test. Statistical significant differences ($\alpha<0.05$) are indated with * in the figure.
Figure 1:
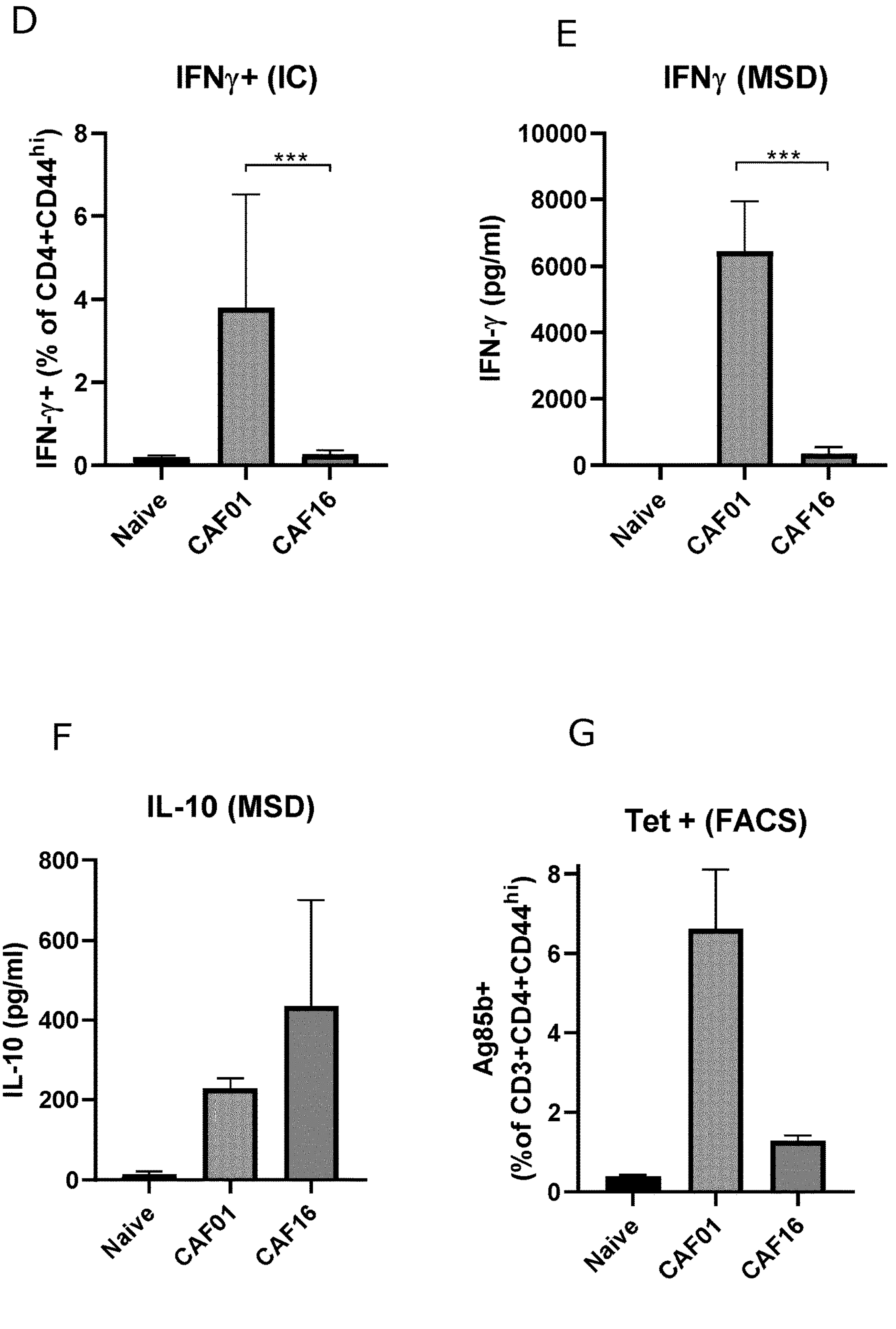
Figure 1:
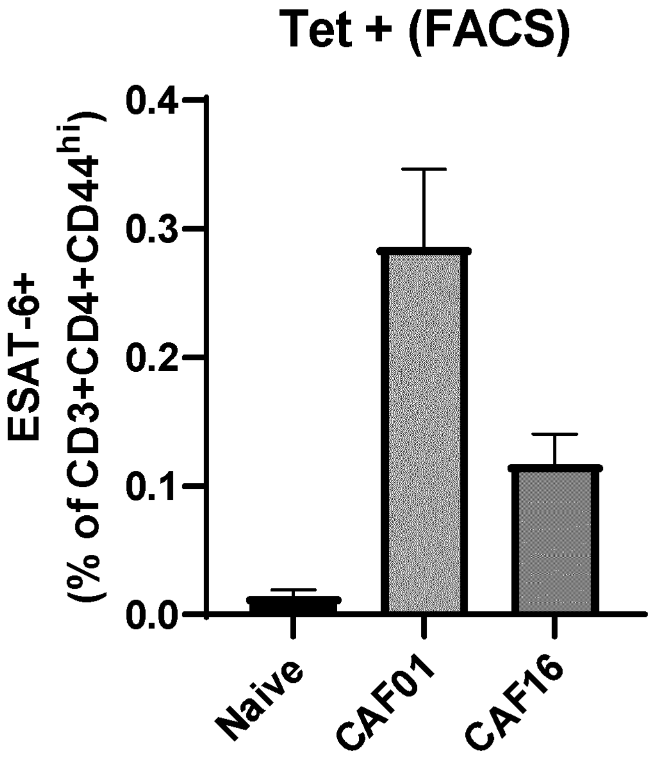

The present invention will now be described in more detail in the following.

DETAILED DESCRIPTION OF THE INVENTION

Definitions

Prior to discussing the present invention in further details, the following terms and conventions will first be defined:

Adjuvants

In the present context, the term "Adjuvants" refers to a compound or mixture that stabilizes the composition and/or facilitates transfection of cells with the composition or a compound that enhances the immune response to an antigen. An adjuvant can serve as a tissue depot that slowly releases the antigen and as a lymphoid system activator, which non-specifically enhances the immune response. Often, a primary challenge with an antigen alone, in the absence of an adjuvant, will fail to elicit a humoral or cellular immune response.

All-Trans Retinoic Acid (ATRA)

In the present context, the term "ATRA" refers to all-trans retinoic acid, a lipophilic metabolite of vitamin A, which has been shown to inhibit the Th17 polarization while enhancing FoxP3 expression (Elias_2008, Kwok_2012) and to operate directly on T cells via reduction of RORγT (Mucinda_2007).

All-Trans Retinoic Acid (ATRA) Analogues

In the present context, the term "ATRA analogues" refers to ligands targeting similar receptors as ATRA, including retinoic acid receptors and retinoic acid-related orphan receptors.

Anergic T Cell

In the present context, the term "anergic T cell" refers to a type of T cells that fail to respond to the antigen that they are specific for.

Antigen (Ag)

In the present context, the term "antigen" refers to a molecule that can activate the immune system in a specific manner.

Auto-Antigen (AutoAg)

In the present context, the term "auto-antigen" refers to a molecule coming from the host itself and are able to active the hosts own immune system in a specific manner.

Cationic Adjuvant Formulation (CAF)

In the present context, the term "CAF" refers to a family of adjuvants that are able to trigger a strong Th1 response.

CAF®01

In the present context, the term "CAF01" or "CAF®01" refers to a member of the CAF family. CAF®01 is composed of N,N-dimethyl-N,N-dioctadecylammonium (DDA) and Mincle-receptor agonists Trehalose-6,6-dibehenate (TDB), preferably in a 5:1 ratio (murine dose 250/50 μg DDA/TDB).

CAF®04

In the present context, the term "CAF04" or "CAF®04" refers to a member of the CAF family. CAF®04 is composed of N,N-dimethyl-N,N-dioctadecylammonium (DDA) and glycerolipid monomycolyl glycerol (MMG), preferably in a 5:1 ratio (murine dose 250/50 μg DDA/MMG).

CAF®16

In the present context, the term "CAF16" or "CAF®16" refers to a member of the CAF family. CAF®16 is composed of CAF®01 and ATRA, preferably DDA, TDB and ATRA in a 5:1:6 ratio (murine dose 250/50/300 μg DDA/TDB/ATRA), and preferably cholesterol, more preferably in a 5:1:6:4 ratio (murine dose 250/50/300/200 μg DDA/TDB/ATRA/Cholesterol).

CAF®40

In the present context, the term "CAF40" or "CAF®40" refers to a member of the CAF family. CAF®40 is composed of CAF®04 and ATRA, preferably DDA, MMG and ATRA in a 5:1:6 ratio (murine dose 250/50/300 μg DDA/MMG/ATRA). The adjuvant may include cholesterol, preferably in a 5:1:6:4 ratio (murine dose 250/50/300/200 μg DDA/TDB/ATRA/Cholesterol).

ExTh17

In the present context, the term "ExTH17" refers to CD4 helper T cells that have at some point in history produced IL-17.

FOXP3

In the present context, the term "FOXP3" refers to a transcription factor, which function as a master regulator of the regulatory pathway in the development and function of regulatory T cells.

Th17 Cells

In the present context, the term "Th17 cells" refers to a subset of pro-inflammatory T helper cells defined by their production of IL17.

Immunization

In the present context, the term "immunization" refers to the process, whereby a subject is getting immune or resistant to an infection.

Intradermal

In the present context, the term "intradermal" refers to a way of injecting a substance into the dermis, which is the middle layer of the skin, of a subject.

Intramuscular

In the present context, the term "intramuscular" refers to a way of injecting a substance into the muscles of a subject.

Intravenous

In the present context, the term "intravenous" refers to a way of injecting a substance into the veins of a subject.

MHC Class II Protein

In the present context, the term "MHC class II" refers to one of the primary classes of major histocompatibility complex molecules. MHC class II are found only on professional antigen-presenting cells such as dendritic cells, mononuclear phagocytes and B-cells. Their function is to display fragments derived from cytosolic as well as extracellular protein to either cytotoxic T cells or helper T-cell.

Regulatory T Cells (Treg)

In the present context, the term "Treg" refers to a subpopulation of T cells that modulate the immune system, maintain tolerance to self-antigens and prevent autoimmune diseases. Their effect are mediated mainly by secretion of the cytokine IL10.

RORγT

In the present context, the term "RORγT" refers to a transcription factor, which functions as a master regulator of the development of Th17 cells.

Subcutaneous

In the present context, the term "subcutaneous" refers to a way of injecting a substance into the tissue layer situated under the skin of the subject.

Subject

The term "subject" comprises humans of all ages, other primates (e.g., cynomolgus monkeys, rhesus monkeys); mammals in general, including commercially relevant mammals, such as cattle, pigs, horses, sheep, goats, mink, ferrets, hamsers, cats and dogs, as well as birds. Preferred subjects are humans. The term "subject" also includes healthy subjects of the population and, in particular, healthy subjects, who are exposed to pathogens and in need of protection against infection, such as health personnel.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

The present invention provides a composition comprising CAF®01 or CAF®04, all-trans retinoic acid (ATRA) and an autoimmune antigen for use in prevention or treatment of autoimmune disease.

Further, the present invention disclose an adjuvant that, through simultaneous stimulation through Mincle and Retinoic Acid receptors, prime a regulatory/anergic T cell response or when applied on top of an existing immune response selectively can re-program Ag-specific Th17 cells into exTh17 cells with a regulatory or anergic non-inflammatory phenotype.

The adjuvant is part of the CAF platform developed by Statens Serum Institut. The adjuvant is a further development of the CAF®01 or CAF®04 adjuvants. These adjuvants have been in several pre-clinical and clinical trials and induce high-magnitude Ag specific Th17 responses via the Mincle-Syk-Card9-Bcl10-Malt1 signaling axis when combined with protein or peptide antigens (Schoenen_2010). Incorporation of retinoic acid receptor agonists such as ATRA into CAF®01 (CAF®01+ ATRA=CAF®16) or CAF®04 (CAF®04+ ATRA=CAF®40) direct this otherwise pro-inflammatory Th17 response into a more anti-inflammatory response.

ATRA has previously been associated with deletion of Th17 cells for use against autoimmune diseases (Elias_2008), however, this has been seen as a general immunosuppressed.

This invention describes how using CAF®16 in combination with a specific antigen, are able to only affect the Th17 population, which is specific for the antigen used with CAF®16 without affecting the whole Th17 cell population.

Further, in addition to treat an existing autoimmune disease, the invention can be used as prophylactic vaccine, preventing an autoimmune disease to develop. Using technologies based on DNA- and immune profiling, it is possible to identify patients at risk of developing autoimmune disease. Therefore, it might be possible to prevent development of e.g. MS by applying AAg specific immunoprophylaxis that can prevent the induction of AAg specific effector T-cells by priming this T cell repertoire into a regulatory phenotype.

CAF®16 in combination with MS associated antigens, such as myelin basic protein (MBP) or proteolipid protein (PLP) or more personalized antigen cocktails defined by genome sequencing and/or large-scale T cell epitope profiling, can thus be used to reprogram those Th17 cells recognizing the AutoAgs into regulatory T cells. This could thus inhibit autoimmune inflammation and be used as a prophylactic vaccine in people, where the diseases run in the family. By redirecting myelin sheath specific Th17 cells into regulatory T cells, CAF®16 may prevent pathogenic T cells from destroying the myelin sheath. It is envisaged that this can prevent the onset of disease, with the hope for completely preventing MS. In RA, those would include N-acetylglucosamine-6-sulfatase (GNS) and filamin A (FLNA) amongst others (Mewar_2001).

Injection of CAF®16 together with a defined autoantigen can thus prevent the evolvement of the autoimmune disease.

However, the prophylactic strategy is not possible for all autoimmune diseases. For many autoimmune diseases, patients develop a personalized AAg repertoire and effective screening is therefore often not possible until onset of disease symptoms. This is e.g. the case for RA, which on the other hand is a relatively slowly progressing disease that may be stopped with an early immunotherapeutic intervention transdifferentiating the disease-causing immune cells. The autoimmunity field has recently, inspired from the cancer field, launched ambitious programs applying methods like genome sequencing and large-scale T cell epitope profiling, which makes it feasible to map disease causing AAg specific T cells in individuals, and thus design personalized immunotherapeutics. From these programs, it has e.g. been shown, that the antigens targeted by the immune system may derive from posttranslational modifications creating neoepitopes to which there is no immune tolerance. Such neoepitopes have been observed in type 1 diabetes, systemic lupus erythematosus, glomerulonephritis, multiple sclerosis and rheumatoid arthritis. Such observations permit specific targeting of the disease causing T cell populations and opens for treatment strategies involving personalized neoepitope based immunotherapies against autoimmune diseases in the near future.

On the basis of the results from CAF®16, the inventors have found that CAF®16 together with a defined autoantigen can be used as either a prophylactic or therapeutic treatment against autoimmune diseases where Th17 cells play a role, and act by specifically inhibiting the Th17 cells causing the disease.

An advantage of the present invention is that the composition is able to specifically inhibit, eliminate or transdifferentiate those Th17 cells that are AutoAg specific for the given disease.

Another advantage of the present invention is that the composition, when affecting those Th17 cells that are AutoAg specific, does not inhibit the protective Th17 cells, leaving the treated subject with a fully functional immune system.

Thus, a first aspect of the present invention relates to a composition comprising DDA, TDB and/or MMG, retinoic acid or analogues thereof, and at least one autoimmune antigen for use in prevention or treatment of an autoimmune disease.

In one embodiment, the composition comprises DDA, TDB, MMG, retinoic acid or analogues thereof, and at least one autoimmune antigen.

In one embodiment, the composition comprises DDA, TDB, retinoic acid or analogues thereof, and at least one autoimmune antigen.

In a further embodiment, the composition comprises DDA, MMG, retinoic acid or analogues thereof, and at least one autoimmune antigen.

In a further embodiment, the composition further comprises cholesterol, preferably the composition comprises of 500-4000 μg/ml cholesterol, more preferably in an amount of 1000-3000 μg/ml cholesterol, most preferably in an amount of 2000 μg/ml cholesterol.

In yet another embodiment, the composition comprises of 1000-4000 μg/ml DDA, preferably in an amount of 2000-3000 μg/ml, more preferably 2500 μg/ml DDA.

In yet a further embodiment, the composition comprises of 100-1000 μg/ml TDB, preferably in an amount of 300-700 μg/ml TDB, more preferably 500 μg/ml TDB.

In another embodiment, the composition comprises of 100-1000 μg/ml MMG, preferably in an amount of 300-700 μg/m MMG, more preferably 500 μg/ml MMG.

In a further embodiment, the composition according to the invention comprises 2500 μg/ml DDA, 500 μg/ml TDB and/or 500 μg/ml MMG.

As seen in example 3, different ATRA analogues were tested as alternatives to ATRA in the composition.
The table below shows the different analogues used as well as ATRA.
| Compound | Structure | |
|---|---|---|
| ATRA | 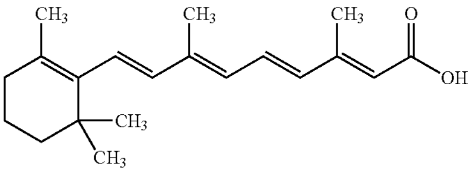 [SMILES: CC1=C(/C=C/C(C)=C/C=C/C(C)=C/C(=O)O)C(C)(C)CCC1] | Agonist for RARα, RARβ and RARγ receptors |
| AC 261066 | 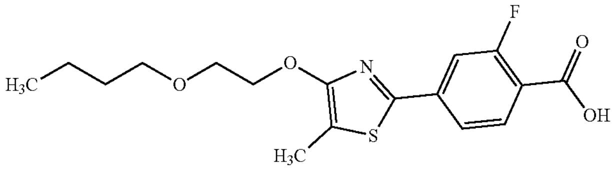 [SMILES: CCCCOCCOc1nc(-c2ccc(C(=O)O)c(F)c2)sc1C] | Agonist for RAR-beta2 |
| SR1001 | 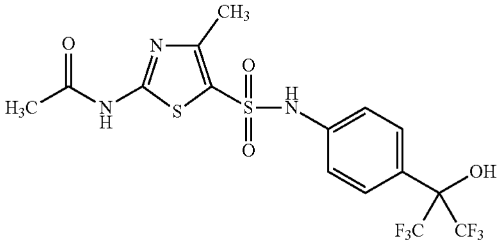 [SMILES: CC(=O)Nc1nc(C)c(S(=O)(=O)Nc2ccc(C(O)(C(F)(F)F)C(F)(F)F)cc2)s1] | RORα/γ inverse agonist |
| CD1530 | 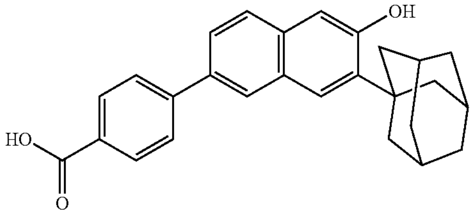 [SMILES: O=C(O)c1ccc(-c2ccc3cc(O)c(C45CC6CC(CC(C6)C4)C5)cc3c2)cc1] | RAR-gamma agonist |
| ML209 | 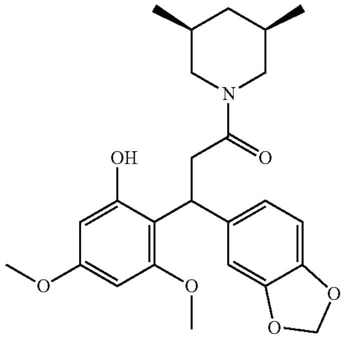 [SMILES: COc1cc(O)c(C(CC(=O)N2C[C@H](C)C[C@H](C)C2)c2ccc3c(c2)OCO3)c(OC)c1] | ROR-gamma inverse agonist |
| XY018 | 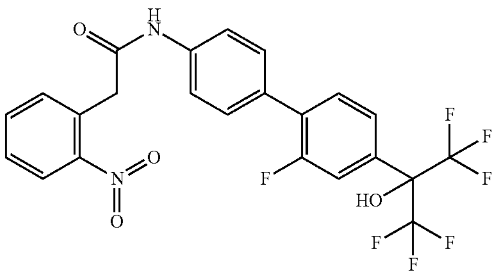 [SMILES: O=C(Cc1ccccc1[N+](=O)[O-])Nc1ccc(-c2ccc(C(O)(C(F)(F)F)C(F)(F)F)cc2F)cc1] | ROR-gamma antagonist |

Thus, in one embodiment, retinoic acid analogues (ATRA) are selected from a group consisting of AC261066, SR1001, CD1530, ML209 and XY018.

In another embodiment, the composition comprises of one or more retinoic acid analogues, such as two retinoic acid analogues, such as three retinoic acid analogues.

In another embodiment, the composition comprises the retinoic acid or retinoic acid analogues in an amount of 1000-5000 μg/ml, preferably 2000-4000 μg/ml, more preferably 3000 μg/ml.

A second aspect of the invention relates to a composition comprising retinoic acid or analogues thereof, and at least one autoimmune antigen for use in prevention or treatment of autoimmune diseases.

The immune system normally protect the subject from foreign cells. Autoimmune diseases develop when the immune system by mistake starts a reaction against the body's own cells.

The autoimmune diseases as described within this invention is characterized by being driven by Th17 cells.

Thus, in one embodiment, the autoimmune disease treated according to the invention is an autoimmune disease driven by Th17 cells, i.e. a Th17 cell mediated autoimmune disease.

In another embodiment, the autoimmune disease treated according to the invention is selected from the group consisting of Rheumatoid arthritis (RA), Multiple Sclerosis (MS), Systemic Lupus Erythematosus (SLE), Juvenile idiopathic arthritis (JIA), Sjögren syndrome, Systemic Sclerosis (SSc), ankylosing spondylitis (AS), Type 1 Diabetes (T1D), Alzheimers disease, Autoimmune thyroid diseases (AITD), such as Graves' disease and Hashimoto's disease, Myasthenia Gravis, Inflammatory Bowel Diseases (IBDs), such as Crohn's disease and ulcerative colitis and Psoriasis. Preferably, the autoimmune diseases treated according to the invention is Rheumatoid arthritis (RA) or Multiple Sclerosis (MS).

In a further embodiment of the present invention, the autoimmune antigen is selected from the group consisting of Collagen II, rp123a, MOG, MOG (1-125) and MOG (35-55).

For an autoimmune disease to develop, the Th17 cells has to be stimulated by an autoantigen.

A method of prevention or treatment of an autoimmune disease in a subject in need thereof, wherein the composition according to the present invention is administered to the subject.

A method of prevention or treatment of an Th 17 cell mediated autoimmune disease in a subject in need thereof, wherein the composition according to the present invention is administered to the subject.

The method of prevention or treatment of an autoimmune disease according to the present invention, wherein the autoimmune disease is selected from the group consisting of Rheumatoid arthritis (RA), Multiple Sclerosis (MS), Systemic Lupus Erythematosus (SLE), Juvenile idiopathic arthritis (JIA), Sjögren syndrome, Systemic Sclerosis (SSc), ankylosing spondylitis (AS), Type 1 Diabetes (T1D), Autoimmune thyroid diseases (AITD) such as Graves' disease and Hashimoto's disease, Myasthenia Gravis, Inflammatory Bowel Diseases (IBDs) such as Crohn's disease and ulcerative colitis and Psoriasis, preferably the autoimmune diseases is Rheumatoid arthritis (RA) or Multiple Sclerosis (MS).

By applying the same autoantigen in the composition according to the invention, the autoantigen-specific Th17 cells can be targeted.

Thus, in one embodiment, the autoantigen is a Th17 stimulating auto-antigen.

In another embodiment, the autoantigen is an IL17 stimulating auto-antigen.

In a further embodiment, the autoantigen is an antigen capable of inducing an autoimmune disease.

In yet another embodiment, the autoantigens are selected from the group consisting of autoantigens such as, but not limited to, collagen II (P02458), 60S ribosomal protein L23a, IX (P20849) and XI (P12107), A3 (P05067), guanosine diphosphate-1-fucose synthase (Q13630), myelin basic protein (P02686), myelin oligodendrocyte glycoprotein (Q16653), anoctamin-2 (Q9NQ90), zinc transporter-8 (ZnT8) (Q8IWU4), pancreatic duodenal homeobox factor 1 (PDX1) (P52945), chromogranin A (CHGA) (P10645), islet amyloid polypeptide (IAPP) (P10997), Ro (P10155), La (P05455), SIRT-1 (Q96EB6), double-stranded DNA, proteoglycan (PG or aggrecan), vimentin (P08670), filaggrin (P20930), fibrinogen (P02671 and P02675), heat shock proteins (HSP) (P08238), nuclear proteins and citrullinated and other modified versions of these and other proteins.

The autoantigens also includes patient-specific personalized auto antigens (AAgs) and neoepitopes defined with methods like genome sequencing and large-scale T cell epitope profiling, which makes it feasible to map personal disease-causing AAg specific T cells, and thus design personalized immunotherapeutics similar to the neoepitope-based therapies under investigation in the cancer field. These methods enable specific targeting of the disease-causing T cell populations, and thus avoid immune-related adverse events.

Thus, in one embodiment, the autoantigens includes patient-specific personalized auto antigens (AAgs) and neoepitopes defined with methods like genome sequencing and large-scale T cell epitope profiling.

Administration of compositions can be done in a number of ways as described in the following, non-limiting, examples. By intradermal injection, which is a delivery of the composition into the dermis of the skin, located between epidermis and the hypodermis. Alternatively, the composition can be administered intravenous, which is an administration directly into the blood stream of the subject. Further, administration of the composition intramuscular is an injection into the muscles of the subject. In addition, the composition can be administered subcutaneous, which is under the skin, in the area between the muscle and the skin of the subject. Further, the composition can be administered intratracheal, which is administration directly into the trachea, transdermal, which is administration across the skin, Intracavity administration includes, but is not limited to administration into oral, vaginal, rectal, nasal, peritoneal, or intestinal cavities as well as, intrathecal. (i.e., into spinal canal), intraventricular (i.e., into the brain ventricles or the heart ventricles), intraarterial (i.e., into the heart atrium) and sub arachnoid (i.e., into the sub arachnoid spaces of the brain) administration. Any mode of administration can be used as long as the mode results in the delivery of the composition in the desired tissue, in an amount sufficient to generate a response in a subject in need of such response.

Administration means of the present invention includes; needle injection, catheter infusion, biolistic injections, particle accelerators, needle-free jet injection, osmotic pumps, oral tablets or topical skin cream.

Thus, in an embodiment, composition for use according to invention is administered to a subject by intradermal, intravenous, intramuscular or subcutaneous injection.

The "subject" as described herein is supposed to receive the composition by injection and comprises humans of all ages, other primates (e.g., cynomolgus monkeys, rhesus monkeys); mammals in general, including commercially relevant mammals such as cattle, pigs, horses, sheep, goats, mink, ferrets, hamsters, cats, dogs; and/or birds. Preferred subjects are humans.

Thus, in an embodiment of the present invention, the subject is selected from the group consisting of; humans of all ages, other primates (e.g., cynomolgus monkeys, rhesus monkeys); mammals in general, including commercially relevant mammals, such as cattle, pigs, horses, sheep, goats, mink, ferrets, hamsters, cats and dogs, as well as birds.

In a preferred embodiment, the subject is a human.

The composition as described herein may be administered in doses suitable for preventing or treating an unwanted immune response as described herein and obtaining a sustained protective effect. In a non-limiting example, the composition is administered in up to eight doses given with 1-8 weeks interval prior to onset of autoimmune disease or alternatively as up to four doses with 1-8 weeks interval following onset of autoimmune disease. In another example, the composition is administered as three doses two weeks apart. The treatment schedule may be repeated as necessary.

Thus, in one embodiment, the composition is administered as eight doses.

In another embodiment, the composition is administered as one dose.

In a further embodiment, the composition can be administered in a dose, which can be repeated.

In yet another embodiment, the composition is administered as 20 doses.

The dose used for each administration vary dependent on the antigen and the subject receiving the dose.

In one embodiment, the composition is administered in 4 doses with 14 days interval.

In another embodiment, the composition is administered in 4 doses with 1 week interval.

Following the initial administration as described above, the composition might be re-administered at a later time-point to maintain and ensure a longterm protection of the subject.

In one embodiment, the composition is administered every 6 months, such as every 8 months, such as every 12 months.

In one embodiment, the composition is an administered in a dose of 625/125/750 ug (DDA/TDB/ATRA).

EXAMPLES

Example 1—Material and Methods

The examples (example 2-6) were carried out using the materials and methods as described in example 1.

Materials

Retinoic acid (ATRA), cholesterol (>99%), Trizma hydrochloride (>99%), Chloroform and Bovine Serum Albumin (BSA) were purchased from Sigma-Aldrich (St Louis, MA, USA). DDA and TDB were purchased from NCK A/S (Farum, Denmark).

Tween® 20, Glycerol (85%) and methanol were obtained from Merck KGaA (Darmstadt, Germany). Gibco phosphate-buffered saline (PBS) was purchased from Life Technologies Limited (Paisley, UK). Lympholyte® Mammal Cedarlane solution was purchased from TriChem ApS (Skanderborg, Denmark).

The electrochemiluminescence Meso Scale Discovery (MSD) kit was purchased from Meso Scale Diagnostics (Rockville, MD, USA).

The H56 antigen was kindly provided by the Vaccine Development department (SSI, Copenhagen, Denmark).

cRPMI consisted of RPMI and 10 mM HEPES buffer (Gibco™, Life Technologies) supplemented with 5×10-6 M β-mercaptoethanol (Sigma-Aldrich), 1% (v/v) penicillin/streptomycin (Invitrogen), 1% 100 mM sodium pyruvate (Invitrogen), 1 mM L-glutamine and non-essential amino acids (Invitrogen).

Methods

Preparation of Adjuvants

CAF®01

CAF®01 was prepared using the lipid film hydration method. DDA and TDB were weighed individually and dissolved in chloroform/methanol 9:1 (v/v). The two components were mixed at a mass ratio of 5:1, corresponding to a molar ratio of 89:11. The resulting solution was placed under nitrogen flow for approximately 1 h to evaporate the organic solvents, and the resulting lipid film was dried overnight to remove residual organic solvents. CAF®01 hydration was performed at 60° C. for 15 min with simultaneous homogenization at 26,000 rpm using a 6F SilentCrusher (Biohit, Helsinki, Finland).

CAF®04

CAF®04 was prepared using the lipid film hydration method. DDA and MMG were weighed individually and dissolved in ethanol. The two components were mixed at a mass ratio of 5:1. The resulting solution was placed under nitrogen flow for approximately 1 h to evaporate the organic solvents, and the resulting lipid film was dried overnight to remove residual organic solvents. CAF®04 hydration was performed at 60° C. for 15 min with simultaneous homogenization at 26,000 rpm using a 6F SilentCrusher (Biohit, Helsinki, Finland).

CAF®16

CAF®16 adjuvant consisting of DDA, TDB, ATRA and cholesterol in a 5:1:6:4 ratio (250/50/300/200 μg murine dose) was prepared in the same manner as CAF®01. Both were stored at −18° C. until rehydration. The lipid films were rehydrated in a 10 mM Tris-buffer with 2% glycerol (pH 7.0). CAF®16 hydration was performed at 60° C. for two times 15 min homogenization at 26,000 rpm using a 6F SilentCrusher (Biohit, Helsinki, Finland) and with sonification for 30 s four times with 10 s break between cycles in between and after homogenization.

CAF®40

CAF®40 adjuvant consisting of DDA, MMG, ATRA and cholesterol in a 5:1:6:4 ratio (250/50/300/200 μg murine dose) was prepared in the same manner as CAF®04. Both were stored at −18° C. until rehydration. The lipid films were rehydrated in a 10 mM Tris-buffer with 2% glycerol (pH 7.0). CAF®40 hydration was performed at 60° C. for two times 15 min homogenization at 26,000 rpm using a 6F SilentCrusher (Biohit, Helsinki, Finland) and with sonification for 30 s four times with 10 s break between cycles in between and after homogenization.

Preparation of Vaccines

The vaccines were prepared under sterile conditions at a dose volume of 100 or 200 μl. The H56 antigen (Ag1) (provided by SSI) was first diluted in 10 mM Tris-buffer with 2% glycerol (pH 7.0) and 50 or 100 μl/dose of CAF®01, CAF®04, CAF®16, CAF®40 or buffer was subsequently added to the solution. The vaccines were mixed by vortexing for 10 s every 10th min for 30 min immediately before immunization.

Mice

C57BL/6J female mice (ENVIGO, Huntington, UK), aged 6-8 weeks, were used for both prophylactic and therapeutic experiment setups.

IL-17 reporter mice were made by crossing Il17a$^{tm1.1(icre)}$ $_{Stck}$/J (IL-17cre) mice with the B6.129X1-Gt (ROSA) 26Sor$^{tm1(EYFP)cos}$/J (R26R-EYFP) mice, both purchased from The Jackson Laboratory. The resulting litter are IL17aCreRosa26ReYFP mice (IL-17 reporter mice), in which cells that express or have expressed IL-17 will express yellow fluorescent protein (YFP) detectable with flow cytometry. Animals were between 8 and 17 weeks at experiment start.

All mice were kept at the experimental animal facilities at Statens Serum Institut and handled by authorized personnel only. All experimental work was conducted in accordance with the regulations of the Danish Ministry of Justice and the Danish National Experiment Inspectorate under permit 2017-15-0201-01363 and in compliance with the European Community Directive 86/609 for the care and use of laboratory animals.

Immunizations and Experimental Setup

For the prophylactic experiment setups, mice were immunized s.c. two or three times with two-weeks intervals with a 200 μl dose and 5 μg Ag/dose at the base of the tail. Spleen and blood were harvested on day 10 post the last immunization.

For the therapeutic experimental setup, mice were immunized s.c. two times with two-weeks intervals with a 100 or 200 μl volume and 5 μg Ag/dose plus 125/25 or 250/50 μg DDA/TDB of CAF®01 at the base of the tail for Th17 induction followed by either no further treatment or four immunizations with two-weeks intervals of a 200 μl dose and 5 μg Ag/dose of CAF®16. Partial bleeds were made 10 days after the second and fourth immunization and blood and spleen were harvested 10 days after the last immunization.

Sample Collection and Cell Preparation

The spleens were suspended in RPMI medium (Invitrogen A/S, San Diego, USA). The spleens were forced through a 100 μm nylon cell strainer (BD Falcon) and washed, first with PBS and subsequently with RPMI. The cells were resuspended in 2 ml complete RPMI (cRPMI) medium supplemented with 10% (v/v) Fetal Calf Serum Superior (FCS, VWR-Bie & Berntsen).

The blood was diluted in PBS and added carefully on top of 5 ml Lympholyte® Mammal Cedarlane solution (TriChem ApS, Denmark) to isolate Peripheral Blood Mononuclear Cells (PBMCs). The tubes were then centrifuged for 20 min at room temperature (RT) at 800-1200× g (2200 rpm) and the intermediate cell layer was harvested. The PBMCs were washed with PBS and subsequently with RPMI. The cells were resuspended in 250 μl complete RPMI (cRPMI) medium supplemented with 10% FCS (VWR-Bie & Berntsen).

The cells were counted using a NucleoCounter NC-100 (ChemoMetec, Lillerod, Denmark).

For ELISA and MSD 2*10$^5$ cells/well were stimulated with 1 μg/ml H56 in sterile-Nunc U-bottom Nunclon Delta 96-well surface plates (Thermo Fisher Scientific), and the supernatants were harvested after 72-84 h incubation at 37° C./5% $CO_2$.

IL-17a Enzyme-Linked Immunosorbent Assay (ELISA)

Plates were coated over night at 4° C. with Purified rat anti-mouse IL-17a (BioLegend, clone: TC11-18H10.1) diluted 1:500 in carbonate buffer (SSI Diagnostics, Denmark) and blocked the following day for 1.5 h at room temperature with 200 μl/well PBS with 2% skimmed-milk powder (Natur Drogeriet, Matas, Denmark). The plates were washed in PBS supplemented with 0.05% (v/v) Tween 20. The stimulated cell supernatants were diluted 4 times in PBS with 2% BSA and applied to the plates together with the IL-17a standard (BioLegend) with a starting concentration of 2500 μg/ml and incubated for 2 h at room temperature. After washing the plates three times, 100 μl Biotin anti-mouse IL-17a (BioLegend, clone: TC11-8H4) diluted 1:2000 in PBS with 1% BSA was added to the plates and incubated for 1 h at room temperature. Following three washes, 100 μl Streptavidin HRP (BD Pharmingen, CA, US) diluted 1:5000 in PBS with 1% BSA was added and the plates were incubated for 30 min at room temperature. After washing the plates four times, TMB substrate was applied with 100 μl/well for approximately 5 minutes in the dark after which the reaction was stopped with 100 μl/well 0.2 M sulfuric acid. The plates were read at 450 nm (correction at 570/or 620 nm) in an TECAN Sunrise™ ELISA reader. Magellan™ v6.6 software (TECAN) was used to obtain the data and the IL-17a concentration was calculated from the standard curve.

Meso Scale Discovery (MSD) Assay

In addition to ELISA, the concentrations of secreted cytokines in the supernatants were measured using the MSD® U-Plex® Biomarker Group 1 (mouse) Multiplex Assays (Meso Scale Diagnostics, Rockville, MD, USA). A plate used to measure IFN-γ, IL-10 and IL-17a was prepared by mixing each linker with its corresponding biotinylated antibody for 1 h at room temperature with stop solution (MSD® U-Plex® kit) added during the last 30 min of the incubation period. The plate was coated with the linker-antibody solution for 1 h with shaking at room temperature. A volume of 25 μl of the supernatants was added to each well containing 25 μl Diluent 41, and the plate was incubated for 1 h at room temperature. Calibrators 5 and 7 was included on the plate as standards. After washing the plate with PBS supplemented with 0.05% (v/v) Tween 20, detection antibody solution (MSD® U-Plex® kit) diluted in Diluent 45 (MSD® U-Plex® kit) was added to each well, and the plate was incubated for 1 h with shaking. Read buffer T was added to the plate before measuring the electrochemiluminescence using a Meso Sector Imager 2400 plate reader equipped with Discovery Workbench 4.0. MSD software (Meso Scale Diagnostics).

Flow Cytometry

Surface and tetramer staining was performed on 2*10$^6$ spleenocytes/well by staining with 50 μl/well MHC II tetramers ESAT-6-APC (1:80) and Ag85b-Bv421 (1:80) both kindly provided by the NIH Tetramer Core Facility together with α-murine CD16/CD32 “Fc Block” (BD) (1:200) in FACS buffer for 30 min at 37° C. After washing the plate twice in FACS buffer, the cells were resuspended in a surface staining mix consisting of α-murine CD3-FITC (1:200, eBioscience), α-murine CD4-Bv786 (1:600, clone GK1.5, BD), Fixable Viability Dye on eF780 (1:500, eBioscience) and α-murine CD44-PE (1:200, BD) for 20 min at 4° C. in the dark. Following two washes in FACS buffer, the cells were resuspended in 200 μl FACS buffer and run on BD LSRFortessa™ Flow Cytometer (BD Biosciences).

Intracellular staining was performed on 1*10$^6$ spleenocytes/well stimulated with the antigen (final concentration 1 μg/ml), anti-CD28 and anti-CD49d antibodies (final concentration each 1 μg/ml) (BD Pharmingen, CA, US) in cRPMI medium with 10% FCS (VWR-Bie & Berntsen) for 1 hour at 37° C. in a C02-incubator. Brefeldin A (BFA, Biolegend) was diluted in cRPMI medium with 10% FCS and added to each well to a final concentration of 5 μg/ml. The plate was incubated for 6 h at 37° C. in ThermostatPlus heatblock (Eppendorph). The plate was washed in FACS buffer consisting of PBS with 1% FCS (VWR-Bie & Berntsen). The cells were stained with 50 μl/well of α-murine CD4-Bv786 (1:600, clone GK1.5, BD), α-murine CD44-FITC (1:600, eBioscience) and Fixable Viability Dye on eF780 (1:500, eBioscience) (1:500) for 20 min at 4° C. in the dark. After two washes in FACS buffer, the cells were fixed and permeabillized with a Cytofix/Cytoperm Kit (BD Pharmingen, CA, US) for 20 min at 4° C. in the dark. Following two washes in Perm wash (BD Pharmingen, CA, US), the cells were stained with α-murine IFN-γ-PE-Cy7 (1:200, clone XMG1.2, eBioscience), α-murine TNF-α-PE (1:200 clone MP6-XT22, eBioscience), α-murine IL-2-APC (1:200, clone JES6-5h4, eBioscience) and α-murine IL-17α-PerCP-Cy5.5 (1:200, eBioscience) for 20 min at 4° C. in the dark. Following three washes in Perm wash, the cells were resuspended in FACS buffer and run on BD LSRFortessa™ Flow Cytometer (BD Biosciences).

The data was analyzed with the FlowJo™ Software v.10.7.1 (BD FlowJo).

Statistical Analysis

Statistical analysis were performed using the GraphPad Prism software v.8.3.0 (GraphPad, La Jolla, CA, USA) with the analysis specified in the figures. A p-value<0.05 was considered statistically significant.

Example 2—Cytokine Responses with and without ATRA

Aim

The aim of this study is to investigate the effect of CAF®01+Ag, with and without ATRA on the inflammatory T cells response.

Material and Methods

Spleenocytes from female C57BL/6 mice were harvested 10 days post s.c. immunizations with two times 200 μl vaccine dose and 5 μg Ag/dose. Cytokine production was measured with intracellular flow cytometry (IC) of cells stimulated for 6 h with the Ag or with electrochemo-luminiscence assay by MSD of supernatants from splenocytes restimulated with Ag for three days (FIG. 1A). IC and MSD was carried out as described in example 1.

Results

IL17a and IFN-gamma were highly elevated in mice treated with CAF®01+Ag compared with naïve mice, whereas in mice treated with CAF®16+Ag the IL17a and IFN-gamma were unchanged compared to the naïve mice. This was the case for both intracellular was well as secreted IL17a and IFN-gamma (FIG. 1B-E).

For IL-10, the treatment with CAF®01+Ag led to a small increase in secreted cytokine, whereas treatment with CAF®16+Ag resulted in high IL10-secretion compared both to naïve- and to CAF®01+Ag-treated mice (FIG. 1F).

Further, the mice were analyzed for specific immune response against the Ag used for immunization. Both CAF®01+Ag and CAF®16+Ag induced a response as seen by an increase in Ag specific CD4 cells measured by Tet expression (FIG. 1G+H).

Statistical analysis was performed using an unpaired Mann-Whitney t-test. Statistical significant differences (α<0.05) are indicated with * in the figure.

Conclusion

In conclusion, incorporation of ATRA in CAF®01 (CAF®16) completely abrogates inflammatory Th1 and Th17 inflammatory responses and increases anti-inflammatory IL-10 but does not abrogate Ag specific T cell induction.

Example 3—Cytokine Responses with Different ATRA-Analogues

Aim

The aim of this study is to investigate the effect of CAF®01+Ag, with different ATRA-analogues on the inflammatory T cells response.

Material and Methods

Spleenocytes from female C57BL/6 mice were harvested 10 days post s.c. immunizations with two times a 200 μl vaccine dose and 5 μg Ag/dose measured with intracellular flow cytometry (IC) of cells stimulated for 6 h with the antigen or with electrochemo-luminiscence assay by MSD of supernatants from splenocytes restimulated with Ag for three days (FIG. 1A).

The following ATRA-analogues was used: AC261066, SR1001, CD1530, XY018 and ML209. The ATRA analogues was prepared similar to CAF®16 as described in example 1.

Results

Figure 2:
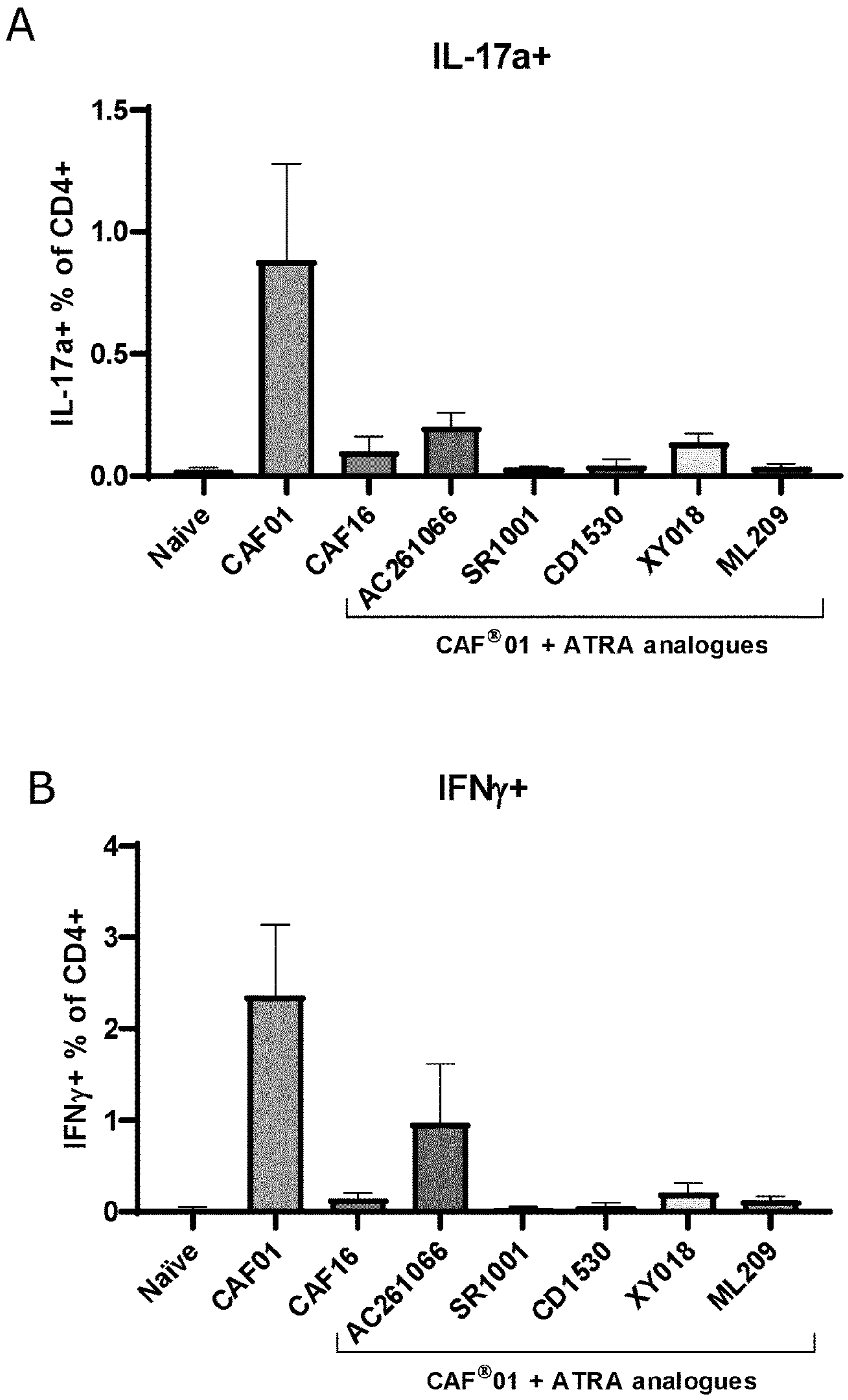
FIG. 2 shows that incorporating different ATRA-analogues in CAF®01 abrogates inflammatory Th1 and Th17 cell responses but not Ag specific T cells. Spleenocytes from female C57BL/6 mice harvested 10 days post s.c. immunizations with two times 200 μl 5 μg Ag/dose vaccine measured with intracellular flow cytometry (IC) of cells stimulated for 6 h with the antigen or with electrochemoluminiscence assay by MSD of supernatants from splenocytes restimulated with Ag for three days. A) IL-17a (IC), B) IFN-γ (IC), C) IL-10 (MSD), D) MHCII tetramers surface staining on antigen-specific cells.
Figure 2:
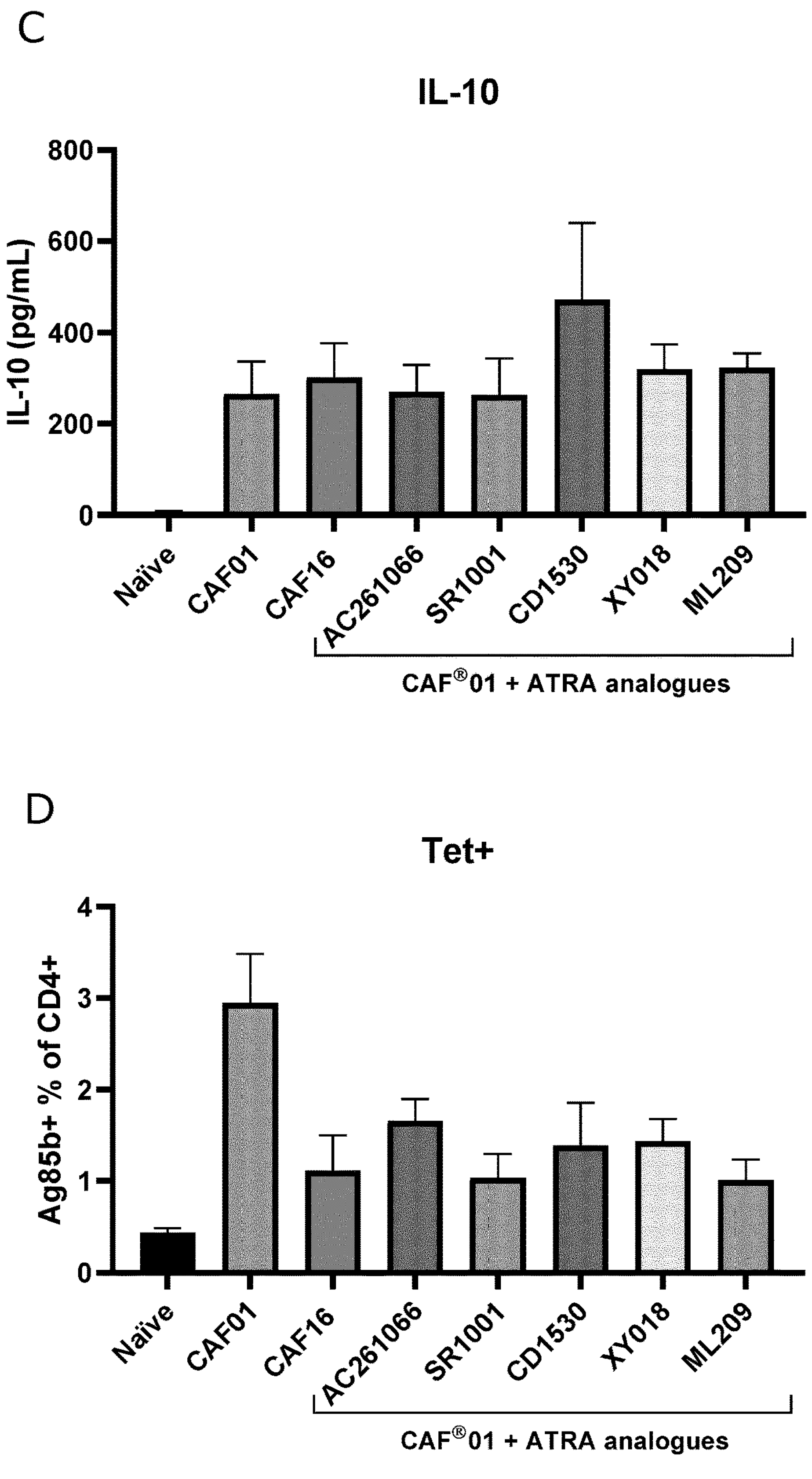

None of the ATRA-analogues induced IL17a or IFN-gamma production in the CD4+ cells in contrast to CAF®01+Ag stimulation, which induced a high production of both cytokine compared to cells from naïve mice (FIG. 2A+B). The IL-10 secretion seen after stimulation with the ATRA-analogues was similar to the secretion seen after stimulation with CAF®01+Ag and was strongly induced compared to cells from naïve mice (FIG. 2C).

Further, similar to the results from example 2, the antigen specific T cells were not affected by the use of ATRA analogues (FIG. 2D).

Conclusion

In conclusion, incorporating different ATRA-analogues in CAF®01 completely abrogates inflammatory Th1 and Th17 cell responses and increases anti-inflammatory IL-10 but did not abrogate the Ag specific T cells.

Example 4—Impact of CAF®16 on Established Th17 Responses

Aim

The aim of this study is to see if CAF®16+Ag can abrogate established Th17 responses.

Material and Methods

Figure 3:
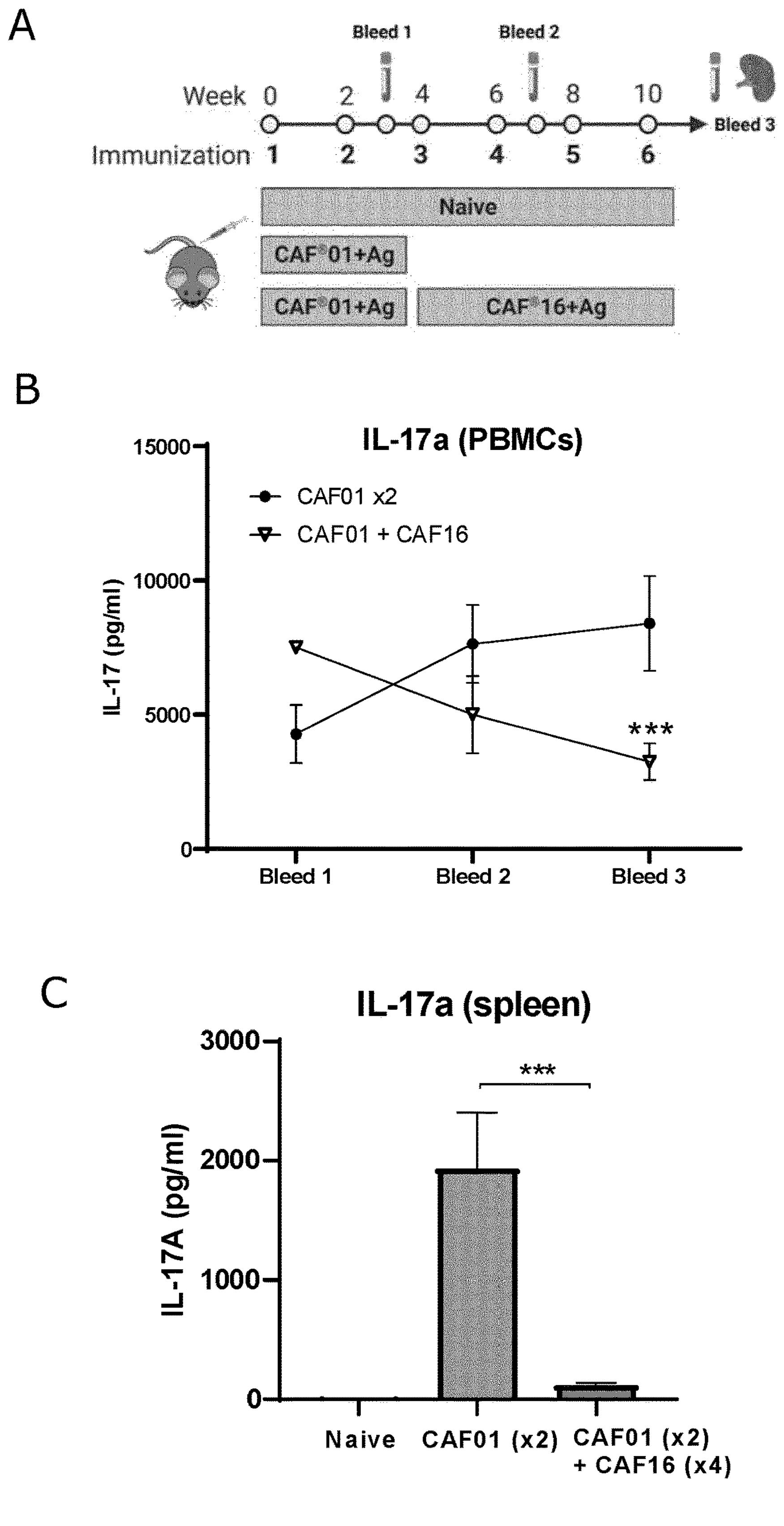
FIG. 3 shows that CAF®16 abrogate existing Th17 responses. A) Experiment setup; female C57BL/6 mice were immunized s.c. with CAF®01+Ag two times or CAF®01+Ag two times followed by four immunizations with CAF®16+Ag with 200 μl vaccine 5 μg Ag/dose (vaccines; n=12, naïve; n=3). Blood was harvested 10 days after every second immunization and spleens were harvested 10 days post the last immunization. B) PBMCs were isolated from the blood and cells were restimulated with Ag for three days and cytokine secretion was measured on supernatants using IL-17a ELISA C) IL-17a ELISA on supernatants from spleenocytes after three days restimulation with Ag. Statistical analysis was performed using a B) paired t-test and C) unpaired t-test. Statistical significant differences ($\alpha<0.05$) are indated with * in the figure.

Female C57BL/6 mice were immunized s.c. with CAF®01+Ag two times or CAF®01+Ag two times followed by four immunizations with CAF®16+Ag with 200 μl vaccine dose and 5 μg Ag/dose (vaccines; n=12, naïve; n=3). Blood was harvested 10 days after every second immunization and spleens were harvested 10 days post the last immunization (FIG. 3A). PBMCs were isolated from the blood and cells were restimulated with Ag for three days and cytokine secretion was measured on supernatants using IL-17a ELISA (as described in example 1).

Results

There was a high secretion of IL17a in both first and second group of mice treated with CAF®01-Ag compared to naïve mice. The IL17a secretion in the first group of mice, which was only treated with CAF®01+Ag, continued to increase the following 7.5 weeks, Whereas the IL17a secretion was decreasing in the second group, which was subsequently treated with CAF®16+Ag (FIG. 3B). The decrease in IL 17a was further confirmed in the spleen isolated from the mice. Spleen isolated from mice immunized with only CAF®01-Ag showed high IL17a levels compared with naïve mice, whereas mice immunized with CAF®01+Ag followed with CAF®16+Ag had IL17a production at the same level as naïve mice (FIG. 3C).

Conclusion

In conclusion, CAF®16+Ag is able to abrogate existing Th17 responses.

Example 5—Redifferentiation of Th17 Cells in IL-17A Fate Reporter Mice

Aim

The aim of this study is to test how the CAF®16-Ag immunization affects Th17 cells.

Material and Methods

Figure 4:
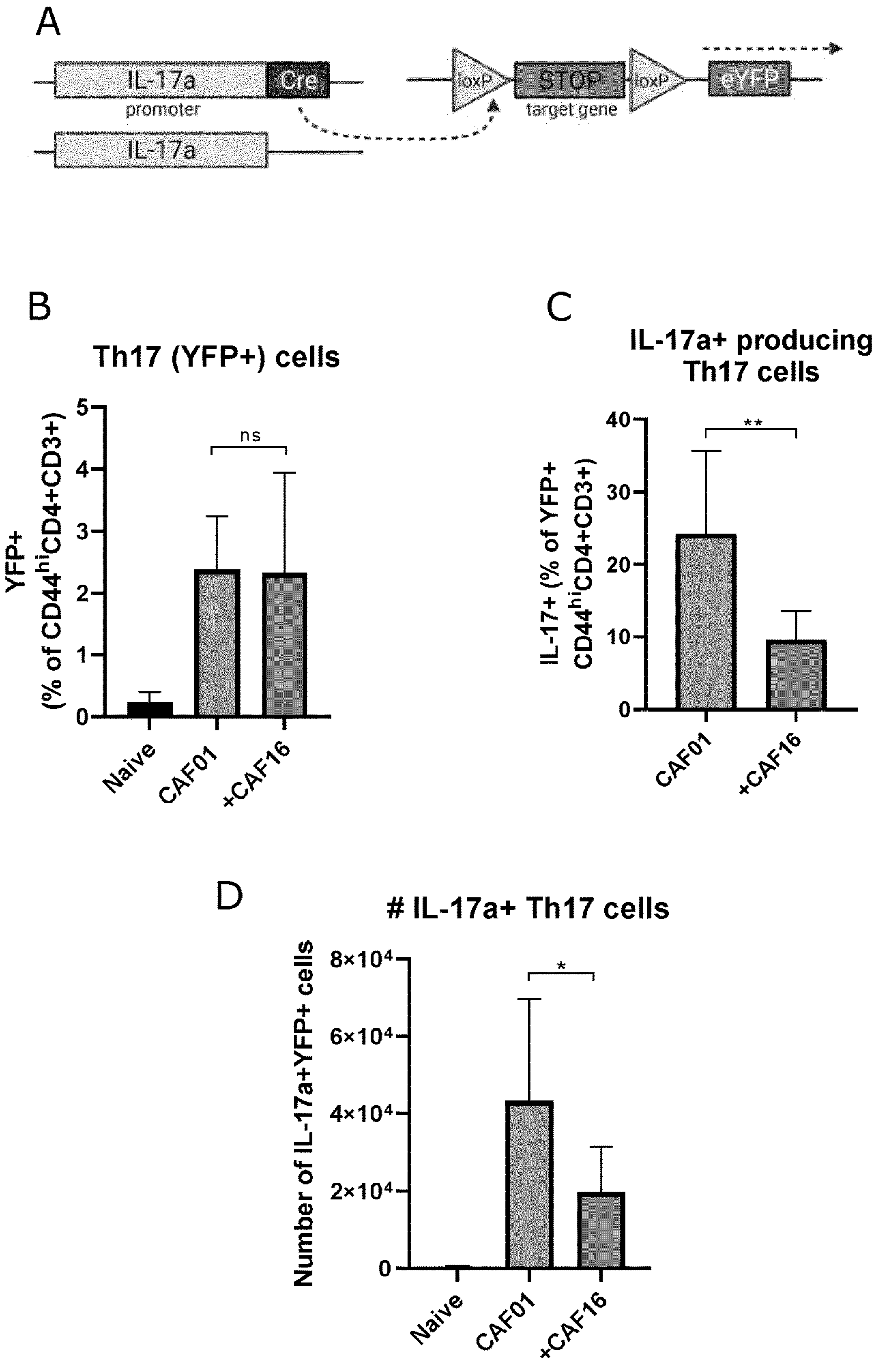
FIG. 4 shows that Th17 cells tagged with yellow fluorescent protein (YFP) in IL-17 reporter mice produce significantly less IL-17a after CAF®16 immunizations. A) reporter mouse strain where one allele transcribes into Cre RNA (later Cre protein) that recognizes and cuts both loxP sites removing the STOP gene and allowing Yellow Fluorescent Protein (eYFP) to be transcribed. Cells that have been producing IL-17a at any time over the course of their life-span will express YFP. B) and C) IL-17 reporter mice were immunized s.c. with CAF®01+Ag two times or CAF®01+Ag two times with 100 μl vaccine 5 μg Ag/dose followed by four immunizations with CAF®16+Ag with 200 μl vaccine 5 μg Ag/dose (n=5-8). Spleens were harvested 10 days after the last immunization and measured with flow cytometry. B) YFP+ and thus Th17 cells, C) IL-17+ cells out of YFP+ cells. D) Number of YFP+ cells that still produce IL-17. Statistical analysis was performed using an unpaired Mann Whitney t-test. Statistical significant differences ($\alpha<0.05$) are indicated with * in the figure, while ns is non-significant.

The mouse used is a reporter mouse strain, where one allele transcribes into Cre RNA (later Cre protein) that recognizes and cuts both loxP sites removing the STOP gene and allowing Yellow Fluorescent Protein (eYFP) to be transcribed. Cells that are or have been producing IL-17a at any time over the course of their life-span will permanently express YFP (FIG. 4A). IL-17a fate reporter mice were immunized s.c. with CAF®01+Ag two times or CAF®01+Ag two times with 100 μl vaccine dose and 5 μg Ag/dose followed by four immunizations with CAF®16+Ag with 200 μl vaccine dose and 5 μg Ag/dose (n=5-8). Spleens were harvested 10 days after the last immunization and YFP and IL17a were measured with flow cytometry (as described in example 1).

Results

The number of YFP+ cells is increased in both groups (CAF®01+Ag and CAF®01+Ag followed by CAF®16+Ag) compared to naïve mice and thus Th17 cells have been primed in both groups (FIG. 4B) However, the frequencies of IL17a+ cells amongst YFP+ were significantly lower in the group of mice treated with CAF®16+Ag compared to mice treated with CAF®01+Ag (FIG. 4C). This demonstrates that CAF16 changed the fate Th17 cells to exTh17 cells no longer producing IL-17a.

Conclusion

CAF®16 immunization redirected Th17 cells (YFP+) into non-IL-17α-producing exTh17 cells.

Example 6—IL-17 Response with Different Antigens

Aim

The aim of this study is to see if the inhibitory effect seen by CAF®16 in the previous example is antigen specific and thereby only inhibit the immune response induced by a specific antigen.

Material and Methods

Figure 5:
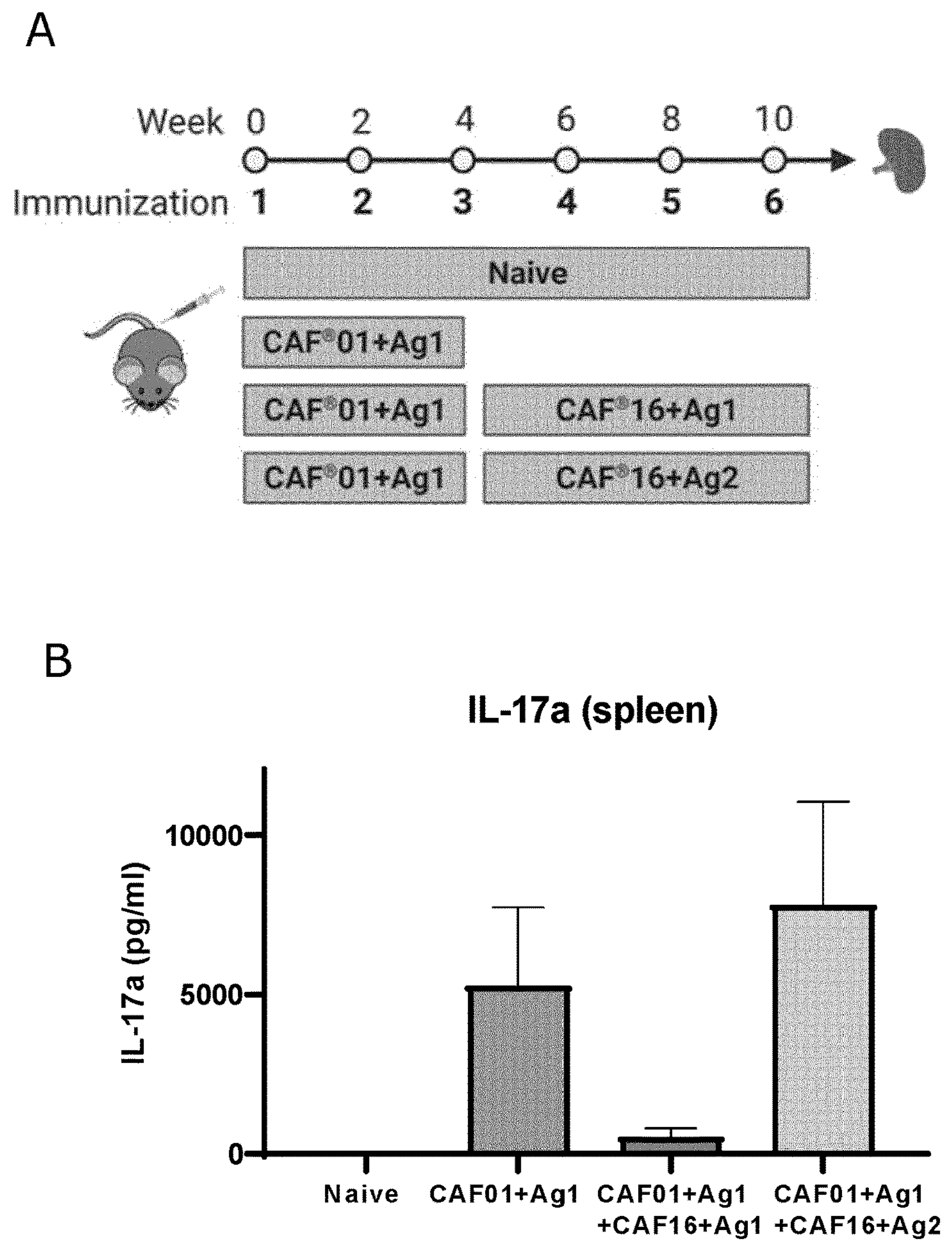
FIG. 5 shows that CAF®16 abrogates an existing Th17 response in an Ag-specific manner. A) Experiment setup; female C57BL/6 mice were immunized s.c. with CAF®01+Ag1 two times or CAF®01+Ag1 two times followed by four immunizations with CAF®16+Ag using either the same Ag (Ag1) or an irrelevant Ag (Ag2) with 200 μl vaccine 5 μg Ag/dose (each group n=8, naïve group, n=4). Spleens were harvested 10 days after the last immunization. B) Spleenocytes were restimulated with Ag1 for three days and cytokine secretion was measured on supernatants using IL-17a ELISA.

Female C57BL/6 mice were immunized s.c. with CAF®01+Ag1 two times or CAF®01+Ag1 two times followed by four immunizations with CAF®16+Ag using either the same Ag (Ag1) or an irrelevant Ag (Ag2) with 200 μl vaccine dose and 5 μg Ag/dose (each group n=8, naïve group, n=4). Spleens were harvested 10 days after the last immunization (FIG. 5A). Spleenocytes were restimulated with Ag1 for three days and cytokine secretion was measured on supernatants using IL-17a ELISA.

Results

Similar to previous examples, mice immunized with CAF®01+Ag1 had high levels of IL17a compared to naïve mice. In addition, mice immunized with CAF®01+Ag1 and subsequently with CAF®16+Ag1 produced IL17a at the same level as naïve mice. Importantly, when the mice was immunized, first with CAF®01+Ag1 and subsequently with CAF®16+Ag2, the level of IL17a was increased compared to mice immunized with only CAF®01+Ag1 (FIG. 5B).

Conclusion

In conclusion, CAF®16 abrogates an existing Th17 response in an Ag-specific manner. Mice subsequently immunized with a CAF®16+a different antigen had an immune response comparable to immunization with CAF®01+Ag only, meaning that the inhibition of the Th17 response seen by CAF®16+Ag is antigen specific.

Example 7—Cytokine Responses when Replacing TDB (CAF®01) with MMG (CAF04)

Aim

The aim of this study is to test if the effect of CAF®16-Ag1 on cytokine production is maintained when replacing TDB with MMG (in the same amount), thus using CAF®04+ ATRA (CAF®40) instead of CAF®01+ ATRA.

Material and Methods

Spleenocytes from female C57BL/6 mice harvested 10 days post s.c. immunizations with two times 200 μl vaccine dose and 5 μg Ag/dose measured with electrochemoluminiscence assay by MSD of supernatants from spleenocytes restimulated with Ag for three days (as described in example 1).

Results

Figure 6:
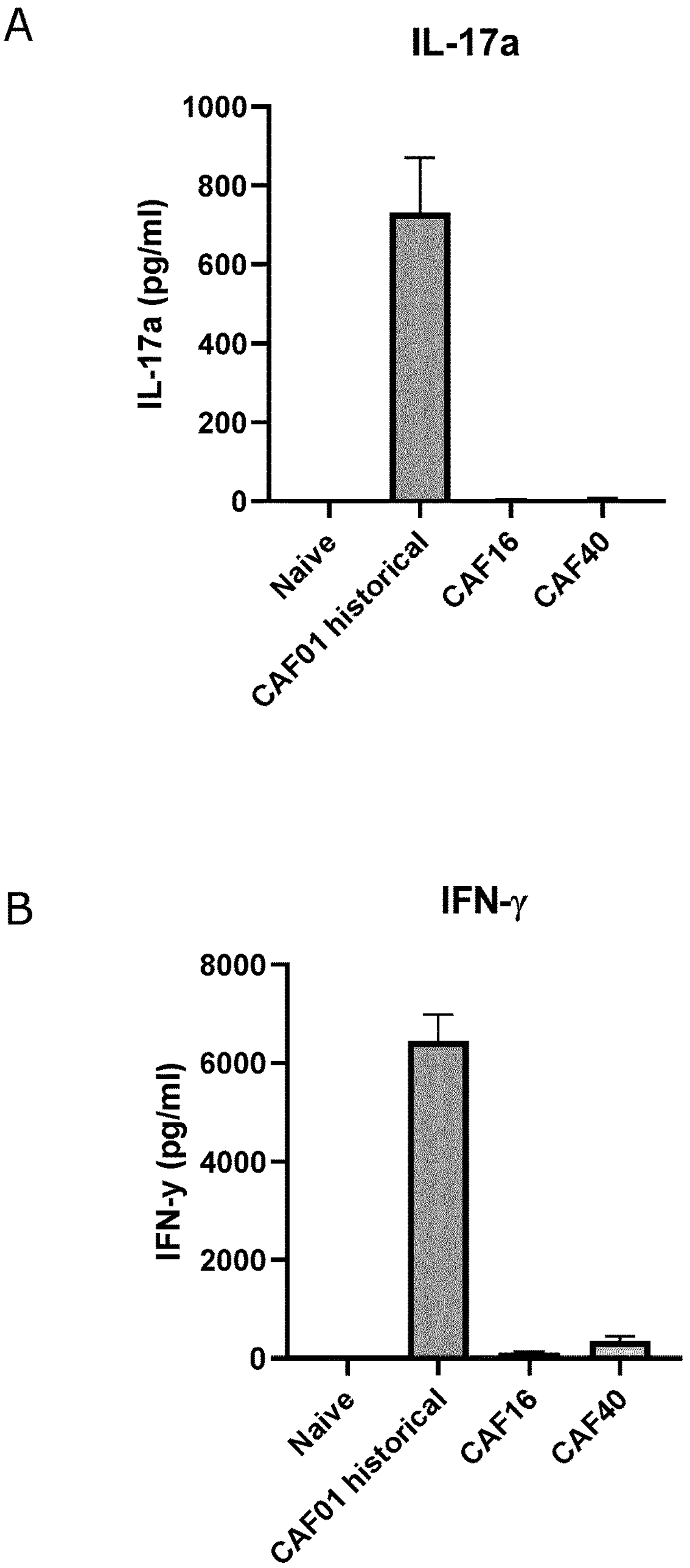
FIG. 6 shows that replacing TDB with MMG (also acting through the MINCLE receptor) also abrogates inflammatory T cell responses. Spleenocytes from female C57BL/6 mice harvested 10 days post s.c. immunizations with two times 200 μl 5 μg Ag/dose vaccine measured with electrochemoluminiscence assay by MSD of supernatants from spleenocytes restimulated with Ag for three days. A) IL-17a, B) IFN-γ.

Both IL17a and IFN-gamma secretion were strongly induced in mice immunized with CAF01+Ag1, whereas in both CAF16+Ag1 and CAF04+ ATRA+Ag1, IL17a and IFN-gamma were almost absent (FIG. 6A+B).

Conclusion

In conclusion, replacing CAF01+ ATRA with CAF04+ ATRA (both acting through the MINCLE receptor) abrogates inflammatory T cell responses to the same level as CAF16-Ag1.

Example 8—Cytokine Responses when Giving CAF®01 Following CAF®16+Ag

Aim

The aim of this study is to test if the effect of CAF®16-Ag1 on cytokine production is maintained when CAF®01 is subsequently added.

Material and Methods

Figure 7:
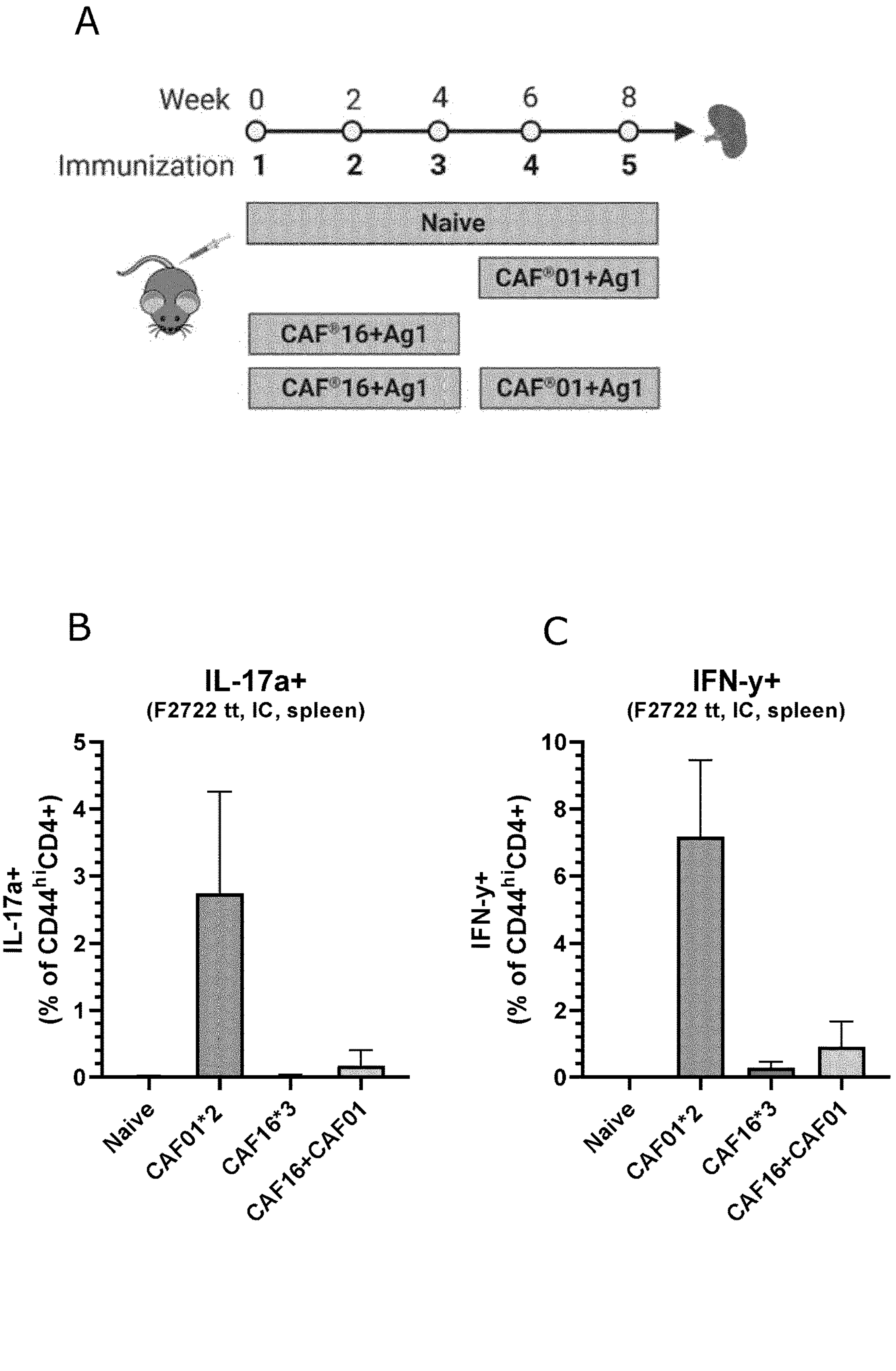
FIG. 7 shows cytokine responses when giving CAF®01 following CAF®16. A) Prophylactic experimental setup; female C57BL/6 mice were immunized s.c. with CAF®16+Ag three times or nothing followed by two immunizations with CAF01+Ag or nothing. (each group n=8, naïve group, n=4). A) and B) Spleenocytes harvested 10 days post last immunization measured with electrochemoluminiscence assay by MSD of supernatants from spleenocytes restimulated with Ag for three days. B) cells positive for IL-17a, C) cells positive for IFN-γ.

Female C57BL/6 mice were either immunized (s.c.) with CAF16+Ag three times or not treated, followed by either two immunizations with CAF01+Ag or nothing (FIG. 7A). Each group of treated mice n=8, naïve group, n=4.

Results

Both IL17a and IFN-gamma secretion were strongly induced in mice immunized with CAF01+Ag1 only, whereas in both groups initially immunized with CAF16+Ag1, IL17a and IFN-gamma secretion was similar to the group of naïve mice (FIG. 7B+C).

Conclusion

In conclusion, CAF®16+Ag was able to inhibit the Th17 response in the mice. The inhibition of Th17 cells was maintained following subsequent stimulation with CAF®01+Ag.

Example 9—CAF®16 in the EAE Murine Model

Aim

The aim of this study is to investigate whether the CAF®16 adjuvant is able to reduce disease in an experimental allergic encephalomyelitis (EAE) autoimmune disease model mimicking Multiple Sclerosis in humans.

Materials and Methods

Active induction of experimental allergic encephalomyelitis (EAE) was induced in C57BL/6J female mice (7-8 weeks) purchased from Jackson Laboratory. EAE experiments were performed at the University of California, San Francisco (UCSF). Complete Freunds Adjuvant (CFA) 4 mg/ml was prepared by mixing Incomplete Freunds Adjuvant (BD Difco™) with *M. tuberculosis* (Clone H37RA from BD Difco™) and vortexed vigorously before use. Myelin Oligodendrocyte Glycoprotein peptide (MOG (35-55), Genemed Synthesis, Inc.) in DMSO was diluted to 1 mg/ml in PBS before use. CFA and MOG (35-55) was mixed 1:1 and emulsified using two syringes connected by a 3-way Nylon Chromatography Stopcock Valve with HDPE Plug (Kimble, Kontes®). EAE induction was performed on day 0 by injection of 50 μl of CFA-MOG emulsion s.c. at four different locations (200 μl per mouse) on the back of the mice under isoflurane anesthesia resulting in 100 μg MOG (35-55) per mouse. Pertussis Toxin (PTx, List Biological) was diluted in PBS and 200 μl was injected i.p. on day 0 and 2 resulting in 200 ng per mouse. Mice were either treated with nothing (n=6) or with CAF®16 with either the MOG (35-55) peptide (n=8) or MOG (1-125) recombinant human protein (rMOG, Anaspec, CA, USA) (n=8) as a 200 μl 25 μg/dose s.c. injection on day 3 and 10 (FIG. 8A). Mice were scored based on their clinical signs in which score 0: clinically normal, 1: weak tail, 2: weak hind limbs, 3: one hind limb paralyzed, 3.5: both hind limbs paralyzed, 4: both hind limbs paralyzed and weak front limbs, 4.5: Both hind limbs and one front limb paralyzed or non-functional movement, 5: Both hindlimbs and both front limbs paralyzed and/or moribund. Mice were scored three times a week until score 2 after which scoring was daily. Mice were provided with gelpacks and moisturized food on the floor of the cage after score 2 and 1 ml pharmaceutical grade saline against dehydration was given to mice after score 3 was reported.

The experiment was terminated at day 21. Spleens were harvested and stimulated with either no antigens, MOG (35-55) or rMOG for three days at 37° C. The supernatants were then harvested and investigated using IL-17a ELISA.

Results

Regardless of the antigen used for administration with the CAF®16 treatment, there was a reduction in the EAE score compared to the control group (FIG. 8B). Furthermore, the area under the curve of the treated groups were statistically different from the control group (FIG. 8C). Independent of the in vitro stimulation, CAF®16 treatment were able to significantly reduce IL-17a response (FIGS. 8D, 8E and 8F).

Conclusion

CAF®16 therapeutic treatment reduced both the disease score and secretion of IL-17a in the experimental allergic encephalomyelitis (EAE) autoimmune disease model mimicking Multiple Sclerosis in humans.

Example 10—CAF®16 in the SKG Mouse Model

Aim

The aim of this study is to investigate if the CAF®16 adjuvant is able to reduce the disease score in the SKG autoimmune mouse model resembling human rheumatoid arthritis. Due to a single point mutation in the ZAP-70 gene, SKG mice have impaired T cell signaling resulting in altered positive and negative selection in the thymus, allowing the escape of polyclonal autoreactive CD4 T cells. These otherwise dormant CD4 T cells require an innate immune stimulus to become activated and cause a destructive arthritis that resembles human rheumatoid arthritis. Their disease development can be synchronized by administering a single i.p. injection with the fungal cell wall component Zymosan (ZymA). Although these mice develop a polyclonal autoreactive TCR repertoire, one endogenous antigen has been identified in this model: the ribosomal protein rp123a. Its role in SKG arthritis is somewhat unclear, but given the limited candidate antigens in SKG arthritis, the inventors used this antigen to couple it with the CAF16 adjuvant in the SKG experiments.

Materials and Methods

SKG mutant mice were kindly provided by UCSF. To synchronize their development of arthritis, Zymosan A (2 mg in PBS) was intraperitoneally injected into 8-16 week old male mice. Zymosan A (Sigma-Aldrich) was dissolved in PBS (DPBS, Gibco) at 10 mg/mL by heating in boiling water for 10 min. Mice were either treated with nothing (n=6) or with CAF16 with either no antigen (n=6) or rp123a (n=6) as a 200 μl s.c. injection on day 3 and day 17 (FIG. 9A). The SKG mice were scored according to the swelling and redness of their digits and joints on each leg. Each affected digit received a 0.1 score and each joint received a 0.5 for a mild and 1.0 for a severely affected joint with swelling and redness resulting in a maximum score of 5.8 per mouse. The experiment was terminated on day 28.

Results

Figure 9C:
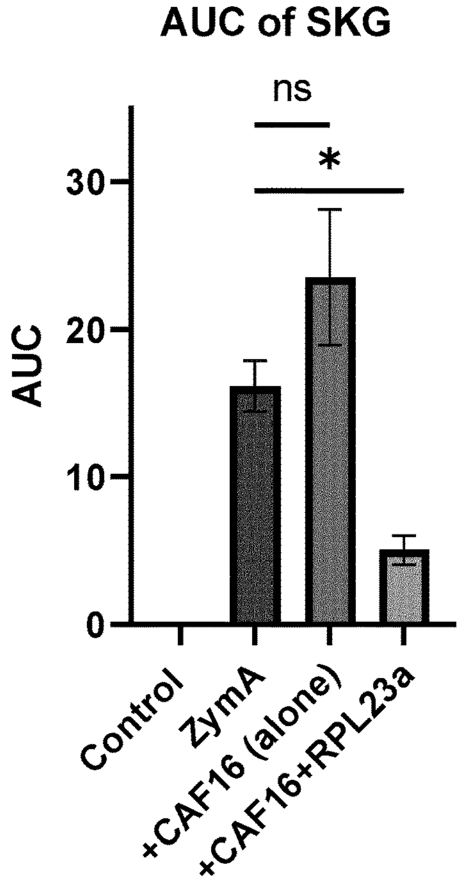
FIG. 9 shows the effect of CAF®16 on disease scores in the SKG autoimmune mouse model resembling human rheumatoid arthritis. A) Zymosan A (ZymA, 2 mg in PBS) was intraperitoneally injected into 8-16 week old male mice on day 0 to induce arthritis development, and PBS was injected in a control group (n=4). Mice were either treated with nothing (n=6) or with CAF®16 with either no antigen (n=6) or with rp123a (n=6) as a s.c. injection on day 3 and day 17. B) SKG disease score. The SKG mice were scored according to the swelling and redness of their digits and joints on each leg. Each affected digit received a 0.1 score and each joint received a 0.5 for a mild and 1.0 for a severely affected joint with swelling and redness resulting in a maximum score of 5.8 per mouse. The experiment was terminated on day 28. C) The area under the curve of the SKG disease scores for the CAF®16-treated groups, a SKG-induced group (ZymA) and a control group (control).

Compared to the ZymA arthritis mice, CAF®16 treatment with rp123a resulted in a reduced SKG arthritis score, whereas CAF®16 administered without an antigen did not (FIG. 9B). There was a significant difference in the area under the curve (AUC) between the non-treated arthritis mice and the mice treated with CAF®16+rp123a (FIG. 9C).

Conclusion

CAF®16 therapeutic treatment reduced the disease score only when administered together with the endogenous antigen rp123a in the SKG arthritis mouse model, which corresponds with previous results showing CAF®16 works in an antigen-specific manner.

REFERENCES

Schoenen_2010_Cutting edge: Mincle is essential for recognition and adjuvanticity of the mycobacterial cord factor and its synthetic analog trehalose-dibehenate. J Immunol; 15; 184(6):2756-60

Elias_2008_Retinoic acid inhibits Th17 polarization and enhances FoxP3 expression through a Stat-3/Stat-5 independent signaling pathway. Blood; 1; 111(3):1013-20

Kwok_2012: Retinoic acid attenuates rheumatoid inflammation in mice. J Immunol; 15; 189(2):1062-71

Mucida_2007: Reciprocal TH17 and regulatory T cell differentiation mediated by retinoic acid. Science; 13; 317 (5835):256-60.

Mewar 2001 Autoantibodies in rheumatoid arthritis: Biomed Pharmacother; 60(10):648-55

The invention claimed is:

1. A method of treatment of an autoimmune disease in a subject in need thereof, the method comprising administering to the subject a composition comprising a) N,N-dimethyl-N,N-dioctadecylammonium (DDA) in an amount of 1000-4000 μg/ml, b) trehalose-6,6-dibehenate (TDB) in an amount of 100-1000 μg/ml, c) cholesterol in an amount of 500-4000 μg/ml, d) retinoic acid or an all-trans retinoic acid (ATRA) analogues thereof selected from a group consisting of AC261066, AM580, SR1001, CD1530, ML209 and XY018, in an amount of 1000-5000 μg/ml, and e) at least one autoimmune antigen which induces the autoimmune disease, wherein the autoimmune disease is selected from the group consisting of Rheumatoid arthritis (RA), Multiple Sclerosis (MS), Systemic Lupus Erythematosus (SLE), Juvenile idiopathic arthritis (JIA), Sjögren syndrome, Systemic Sclerosis (SSc), ankylosing spondylitis (AS), Type 1 Diabetes (TID), Autoimmune thyroid diseases (AITD), Graves' disease, Hashimoto's disease, Myasthenia Gravis, Inflammatory Bowel Diseases (IBDs), Crohn's disease, ulcerative colitis, and Psoriasis.

2. The method according to claim 1, wherein the composition further comprises monomycolyl glycerol (MMG).

3. The method according to claim 1, wherein the composition comprises DDA, TDB, and retinoic acid.

4. The method according to claim 2, wherein the composition comprises DDA, MMG, retinoic acid, and at least one autoimmune antigen.

5. The method according to claim 1, wherein the composition comprises 1000-3000 μg/ml cholesterol.

6. The method according to claim 1, wherein the composition comprises 2000-3000 μg/ml DDA.

7. The method according to claim 1, wherein the composition comprises 300-700 μg/ml TDB.

8. The method according to claim 1, wherein the composition comprises MMG, 300-700 μg/ml MMG.

9. The method according to claim 1, wherein the composition comprises the retinoic acid or ATRA analogues in an amount of 2000-4000 μg/ml.

10. The method according to claim 1, wherein the autoimmune antigen is selected from the group consisting of Collagen II and MOG.

11. The method according to claim 1, wherein the composition is administered to a subject by intradermal, intravenous, intramuscular or subcutaneous injection.

12. The method according to claim 1, wherein the subject is selected from the group consisting of humans of all ages, cynomolgus monkeys, rhesus monkeys, cattle, pigs, horses, sheep, goats, mink, ferrets, hamsters, cats and dogs, as well as birds.

13. The method according to claim 5, wherein the subject is a human.

14. The method according to claim 1, wherein the composition is administered as one dose.

15. The method according to claim 1, wherein the composition is administered in a dose of 625 μg DDA, 125 μg TDB and 750 μg ATRA.

16. The method of claim 1, wherein said autoimmune disease inducing autoimmune antigen is selected from collagen II (P02458), 60S ribosomal protein L23a, IX (P20849) and XI (P12107), A3 (P05067), guanosine diphosphate-1-fucose synthase (Q13630), myelin basic protein (P02686), myelin oligodendrocyte glycoprotein (Q16653), anoctamin-2 (Q9NQ90), zinc transporter-8 (ZnT8) (Q8IWU4), pancreatic duodenal homeobox factor 1 (PDX1) (P52945), chromogranin A (CHGA) (P10645), islet amyloid polypeptide (IAPP) (P10997), Ro (P10155), La (P05455), SIRT-1 (Q96EB6), double-stranded DNA, proteoglycan (PG or aggrecan), vimentin (P08670), filaggrin (P20930), fibrinogen (P02671 and P02675), heat shock proteins (HSP) (P08238).

17. The method of claim 1 wherein said at least one autoimmune antigen has at least one of Th17 stimulating activity and IL17 stimulating activity.

* * * * *